(12) United States Patent
Günther et al.

(10) Patent No.: US 11,464,806 B2
(45) Date of Patent: Oct. 11, 2022

(54) GENETICALLY MODIFIED MESENCHYMAL STEM CELLS EXPRESSING AN IMMUNE RESPONSE-STIMULATING CYTOKINE TO ATTRACT AND/OR ACTIVATE IMMUNE CELLS

(71) Applicant: JunctuCell Biomed Manufacturing GmbH, Hohenbrunn (DE)

(72) Inventors: Christine Günther, Munich (DE); Stefanos Theoharis, Munich (DE); Felix Hermann, Munich (DE); Ralf Huss, Waakirchen (DE)

(73) Assignee: JUNCTUCELL BIOMED MANUFACTURING GMBH, Hohenbrunn (DE)

( * ) Notice: Subject to any disclaimer, the term of this patent is extended or adjusted under 35 U.S.C. 154(b) by 159 days.

(21) Appl. No.: 16/774,495

(22) Filed: Jan. 28, 2020

(65) Prior Publication Data

US 2020/0268802 A1    Aug. 27, 2020

Related U.S. Application Data

(63) Continuation of application No. 15/504,554, filed as application No. PCT/EP2015/068942 on Aug. 18, 2015, now abandoned.

(30) Foreign Application Priority Data

Aug. 18, 2014  (EP) .................................. 14181283

(51) Int. Cl.
| | |
|---|---|
| *A61K 35/28* | (2015.01) |
| *C07K 14/52* | (2006.01) |
| *C12N 5/0775* | (2010.01) |
| *A61K 35/17* | (2015.01) |
| *C07K 14/54* | (2006.01) |
| *C07K 14/555* | (2006.01) |
| *C07K 14/705* | (2006.01) |
| *C07K 16/30* | (2006.01) |
| *A61K 35/12* | (2015.01) |
| *A61K 38/00* | (2006.01) |

(52) U.S. Cl.
CPC .............. *A61K 35/28* (2013.01); *A61K 35/17* (2013.01); *C07K 14/52* (2013.01); *C07K 14/54* (2013.01); *C07K 14/555* (2013.01); *C07K 14/70521* (2013.01); *C07K 16/30* (2013.01); *C12N 5/0663* (2013.01); *A61K 38/00* (2013.01); *A61K 2035/124* (2013.01); *C12N 2510/02* (2013.01)

(58) Field of Classification Search
CPC ........ A61K 35/28; C07K 14/54; C07K 14/52; A61P 35/00; C12N 5/0663
USPC ...................................................... 424/93.21
See application file for complete search history.

(56) References Cited

U.S. PATENT DOCUMENTS

| | | |
|---|---|---|
| 2004/0076622 A1 | 4/2004 | Studeny |
| 2011/0002852 A1 | 1/2011 | Chopp et al. |
| 2014/0271580 A1 | 9/2014 | Garry et al. |

FOREIGN PATENT DOCUMENTS

| | | | |
|---|---|---|---|
| CN | 101778934 A | 7/2010 | |
| CN | 102695517 A | 9/2012 | |
| EP | 1 658 853 A1 | 5/2006 | |
| JP | 2012-523243 A | 10/2012 | |
| WO | WO 2008/150368 A1 | 12/2008 | |
| WO | WO 2015/035235 A1 | 3/2015 | |
| WO | WO-2015112626 A1 * | 7/2015 | ............ C07K 14/54 |
| WO | WO 2016/146819 A1 | 9/2016 | |

OTHER PUBLICATIONS

Nastala , 994, Journal of Immunology, 153:1697-1706.*
Zhang, 2011, Molecular Therapy, 19:751-759.*
Weiss, 2007, Expert Opinion on Biological Therapy, 7:1705-1721.*
Wei, (2013, Journal of Experimental and Clinical Cancer Research, 32:1-7).*
Vom Berg (2013, J. Exp.. Med, 210:2803-2811).*
Shah, Khalid, "Mesenchymal stem cells engineered for cancer therapy," Advanced Drug Delivery Reviews 6 (2012) 739-748.
Hongwei, Xu, et al., "Synergistic Inducement of Proliferation and Anti-Tumor Activity of Human PBMC by IL-12, IL-7 and IL-2 in Vitro", Chinese Journal of Immunology, 1998: 14(5) 338.
Battaglia et al. 2012, "Interleukin-21 (IL-21) synergizes with IL-2 to enhance T-cell receptor-induced human T-cell proliferation and counteracts IL-2/transforming growth factor-b-induced regulatory T-cell development" Immunol, 139: 109-120.
European Business Development Conference Presentation "What is the impact of new technologies and novel therapeutic approaches to fight cancer?" Presented by apceth Applied Cell therapy, Sep. 23, 2013 (in 16 pages).
Gao, et al. 2010 "Therapeutic potential of human mesenchymal stem cells producing IL-12 in a mouse xenograft model of renal cell carcinoma" *Cancer Letters* 290(2): 157-166.
Hu, et al. 2010 "Mesenchymal stem cells: A promising targeted-delivery vehicle in cancer gene therapy" *Journal of Controlled Release* 147(2): 154-162.
Li, et al. 2005 "Cytokines transduced bone marrow stromal ceil lines promote immunohematopoietic reconstitution in mice after allogeneic bone marrow transplantation" *Immunology Letters* 98(2): 216-224.

(Continued)

*Primary Examiner* — Valarie E Bertoglio
(74) *Attorney, Agent, or Firm* — Knobbe, Martens, Olson & Bear, LLP

(57) ABSTRACT

A method of treating a tumor in a subject including administering a genetically modified mesenchymal stem cell (MSC), wherein the MSC includes one or more exogenous nucleic acid molecule(s), wherein the one or more exogenous nucleic acid molecule(s) includes one or more regions encoding two or more immune response-stimulating cytokines operably linked to one or more promoters or promoter/enhancer combinations, wherein the two or more immune response-stimulating cytokines include at least IL-7, and at least one of IL-12 or IL-21.

20 Claims, 9 Drawing Sheets

(56) References Cited

OTHER PUBLICATIONS

Lindner et al. 2010, "Mesenchymal stem or stromal cells: toward a better understanding of their biology?" Transfus Med Hemother, 37:75-83.

Mehrotra et al. 1995 "Synergistic effects of IL-7 and IL-12 on human T cell activation" J. Immunol, 154:5093-5102.

Tsark, et al. 2001 "IL-7 enhances the responsiveness of human T cells that develop in the bone marrow of athymic mice" *The Journal of Immunology* 166(1): 170-181.

Zhao, et al. 2004 "Mechanisms of and perspectives on the mesenchymal stem cell in immunotherapy" *Journal of Laboratory and Clinical Medicine* 143(5): 284-291.

* cited by examiner

A

B

C

D

E

F

G

H

I

J

K

GENETICALLY MODIFIED MESENCHYMAL STEM CELLS EXPRESSING AN IMMUNE RESPONSE-STIMULATING CYTOKINE TO ATTRACT AND/OR ACTIVATE IMMUNE CELLS

FIELD

The invention relates to a genetically modified mesenchymal stem cell (MSC), and their use as a medicament in the treatment of a tumour, said MSCs comprising one or more exogenous nucleic acid molecule(s), wherein said exogenous nucleic acid molecule(s) comprise a region encoding one or more immune response-stimulating or immune response-modulating cytokine(s) operably linked to a promoter or promoter/enhancer combination. The invention further relates to a genetically modified mesenchymal stem cell comprising at least one exogenous nucleic acid molecule that comprises a region encoding an immune stimulatory molecule, for example that that induces T-cell proliferation and/or differentiation.

The invention encompasses the use of MSCs as a medicament in the treatment of a tumour and/or tumour disease, for example by modulating the tumour microenvironment in order to attract immune effector cells and facilitate their activation and/or adoption of a memory phenotype. One aspect of the invention relates to the use of said MSCs in anti-tumour treatment comprising the combined administration of said mesenchymal stem cells with an immunotherapy, for example checkpoint inhibitors, including for example antibodies against CTLA-4, PD-1, PD-L1 and other immune co-stimulatory molecules, immune cells, for example T cells, such as T cells with artificial T cell receptors, for example a chimeric antigen receptor (CAR-Ts) or exogenous T-Cell Receptor (TCR) transduced cells, NK cells or macrophages/monocytes, or active immunotherapeutic drugs, for example, tumour antigens, patient-derived tumour material and other therapeutic drugs aiming to activate and/or direct the immune response against a tumour, or features of a tumour.

BACKGROUND

Mesenchymal stem cells (MSCs) are cells of non-haematopoietic origin that reside in the bone marrow and other tissues. MSCs are commonly considered to be multipotent adult progenitor cells that have the ability to differentiate into a limited number of cell lineages, such as osteoblasts, chondrocytes, and adipocytes. Studies have been conducted on the use of MSCs as a therapeutic entity based on a capacity to differentiate directly into these end-stage phenotypes, including the use of MSCs to promote or augment bone repair and for the repair of cartilage defects (Vilquin and Rosset, Regenerative Medicine 2006: 1, 4, p 589, and Veronesi et al, Stem Cells and Development 2013; 22, p 181). The isolation and cultivation of MSCs for a number of therapeutic indications has been described and represents a promising approach towards treating inflammation-associated disorders (for example WO 2010/119039).

MSCs are known to exhibit immune evasive properties after administration to a patient. MSCs have been shown to exhibit a beneficial immune modulatory effect in cases of transplantation of allogeneic donor material (Le Blanc et al, Lancet 2004: 363, p 1439), thereby reducing a potentially pathogenic alloreactivity and rejection. MSCs treatment can also play a therapeutic role in wound healing. The therapeutic delivery of MSCs can be performed via systemic injection, followed by MSC homing to and engraftment within sites of injury (Kidd et al, Stem Cells 2009: 27, p 2614). MSCs are also known to exhibit migratory properties with respect to homing towards tumours in vivo.

MSC-based cellular therapy using genetically modified MSCs enables the delivery of therapeutic gene products to a specific region of interest in the body of a patient. For example, MSCs have been shown to migrate to areas of inflammation, such as tumours, and thereby locally exert therapeutic influence. MSCs typically have immune-modulatory effects that lead to immune suppression in the area of interest, thereby mediating or reducing inflammation to enhance recovery. However, the present invention makes use of MSCs as a cellular vehicle for the delivery of immunomodulatory effectors for simulating an immune response, thereby utilising the unique homing abilities of MSC to target regions of inflammation, in particular tumours, and thereby exert local therapeutic effects based on activation of an appropriate immune response.

Tumour growth can be countered by appropriate activation or strengthening of an immune response directed against tumour tissue. However, means for local enhancement of such an immune response, without initiating unwanted systemic side effects, are needed in the field of cancer therapy. There are many drugs for the treatment of cancer that cannot be administered systemically without causing significant unwanted side effects (for example fever, elevated levels of liver enzymes or systemic inflammation, such as a cytokine storm, potentially leading to death). One option for avoiding such side effects is the administration of a significantly reduced dose of such drugs, which although effective in reducing side effects, often yields insufficient drug levels at the target site and insufficient therapeutic benefit.

SUMMARY

In light of the prior art the technical problem underlying the present invention is to provide a novel strategy for immunotherapy of cancers. In particular, a problem underlying the invention is the provision of suitable means for local stimulation of an immune response directed against tumour tissue in a subject. A further problem underlying the invention is the provision of means for administration of an effective dose of therapeutic agents, such as immune modulatory or immune stimulatory agents, that provides an effective local effect at the target tissue with reduced levels of unwanted side effects.

This problem is solved by the features of the independent claims. Preferred embodiments of the present invention are provided by the dependent claims.

The invention therefore relates to a genetically modified mesenchymal stem cell for use as a medicament in the treatment of a tumour, wherein said MSCs comprise one or more exogenous nucleic acid molecule(s), wherein said exogenous nucleic acid molecule(s) comprise a region encoding one or more immune response-stimulating cytokine(s) operably linked to a promoter or promoter/enhancer combination, wherein said treatment comprises the combined administration of said mesenchymal stem cells with an anti-tumour immunotherapy.

Combined administration may relate to concurrent and/or sequential administration of said mesenchymal stem cells prior to, during and/or subsequent to said immunotherapy. Combined shall also include a combination treatment regime comprising multiple administrations of either therapeutic component of the treatment. Further embodiments of combined administration are provided herein.

The invention therefore encompasses the medical use of the MSCs described herein, in particular for treating cancer, in addition to methods for the treatment of a subject with a tumour, or methods of treatment of a tumour and/or tumour disease.

The present invention also encompasses the genetically modified mesenchymal stem cells as described herein, as such, independent of their particular medical use.

The present invention enables the stimulation of cells involved in an anti-tumour immune response and thereby the local activation, support and/or strengthening of an anti-tumour immune response. The MSCs as described herein migrate to tumour tissue due to either their natural or an engineered capacity for homing to areas of inflammation in vivo. The homing to and/or engraftment into tumour tissue (tumour stroma) leads to local expression of immune stimulating cytokines, thereby creating increased amounts and/or activities of immune cells in the local tumour environment, thereby enabling the immune system of the patient to attack tumour cells and also providing support for a combined immunotherapy.

The present invention enables an effective and therapeutically relevant dose of one or more immune stimulatory cytokines to be administered via expression from transplanted MSCs while avoiding the significant side effects that are inherent in systemic administration of cytokines without an appropriate targeting agent. The invention therefore relates to the utilization of MSC as a targeting agent and/or vehicle for the local delivery of immune modulatory, preferably immune stimulating signals in regions of inflammation, preferably in and in proximity to tumour tissue.

A crucial limitation in the successful development and clinical use of immunotherapies is the ability of tumours to evade and suppress the natural immune response against the tumour cells, by establishing an immunosuppressive tumour microenvironment, This phenomenon is known as tumour-mediated immunosuppression and is mediated to a large extent by the secretion of anti-inflammatory cytokines by immune cells present in the tumour that display a regulatory phenotype (for example, Regulatory T-cells; TRegs and Monocyte-Derived Suppressor Cells; MDSCs). The invention therefore provides means to modify the tumour microenvironment, making it pro-inflammatory, promoting the activation of immune cells present in the tumour and recruitment and activation of external immune cells and thereby facilitating the broad activation of the immune system against the tumour and/or enhance the efficacy of anti-tumour immunotherapeutic treatments.

In one embodiment the MSCs as described herein can be administered prior to an immunotherapeutic treatment in order to modify and render the tumour microenvironment favourable and conducive to immunotherapies.

The present invention makes use of MSCs as a cellular vehicle for the delivery of immunomodulatory effectors for simulating an immune response, thereby utilising the unique homing abilities of MSC to target regions of inflammation, in particular tumours, and thereby exert local therapeutic effects based on activation of an appropriate immune response, wherein the immune response relates preferably to the natural immune response of a host (subject), and thereby enhance the efficacy and therapeutic effect of immunotherapeutics, such as bi-specific antibodies, adoptive immunotherapies, anti-tumour vaccines and/or checkpoint inhibitors.

MSC are able to express various anti-inflammatory factors in response to pro-inflammatory signals (for example, Transforming growth factor beta (TGF-b), indoleamine 2,3-dioxygenase). For TGF-b it has been shown that it can enhance survival of activated T cells as it protects the cells from so called "activation induced cell death". Surprisingly, the expression of pro-inflammatory cytokines in MSCs allows the targeted and continuous activation of bystander T cells, without inducing activation induced cell death (AICD) in the T cells. This property of the cells described herein is due to the presence of anti-inflammatory factors (e.g. TGF-b) which are also expressed by MSC and prevent AICD. The combination of MSCs expressing anti-inflammatory factors with the pro-inflammatory transgene cytokines leads to an unexpected technical effect that is advantageous in the stimulation of the immune response against tumours.

Surprisingly, the MSCs modified with one or more immune response stimulating cytokine(s) as described herein show unexpectedly good expression and secretion of said cytokines both in vitro and in vivo. A skilled person would not expect that these particular cytokines could be expressed in sufficient quantities and exported from the cells in sufficient quantities to induce or enhance the desired local immune response, based on either the innate response or and immunotherapy.

The invention also encompasses the expression of a combination of immune activating cytokine and/or chemokines in tumours via the MSC-based approach described herein, with the aim to attract immune effector and helper cells, induce immune activation, promote the maturation of memory immune cells and/or suppress the emergence and persistence of suppressive and/or regulatory immune cells.

In one embodiment, a combination of cytokines is used, in order to promote the activation of different arms of the immune response, including the innate and adaptive immune response, effector, helper and/or antigen presenting cells.

It is envisioned that cytokines such as TNF-alpha will activate multiple aspects of the immune system and that this effect may however lack the necessary specificity for an anti-tumoral response.

On the other hand, IL-2, IL-7, IL-15 and IL-21 specifically activate cytotoxic lymphocytes such as T-cells and NK cells that mount a specific response against tumour cells. Likewise, IL-12 will activate cytotoxic lymphocytes, but also monocytes and helper cells.

The combination of IL-12, for example, with IL-2, IL-7, IL-15, and/or IL-21, will have the effect of activating (i) tumour-directed cytotoxic cells, (ii) helper cells that enhance the activation of cytotoxic cells and/or (iii) monocytes that can develop an additive immunological response against the tumour. A combination of cytokines therefore yields synergistic effects, as is seen in the natural immune response, and in the present invention greatly increases the therapeutic efficacy. It was a surprising result that the natural immune response could, in effect, be mirrored, or analogously applied, in an enhanced manner using a MSC-based transgenic approach.

The invention is therefore based on the surprising finding that by providing a combination of transgenes encoding immune response-stimulating cytokine(s) in one or more MSCs a more effective local and safe anti-tumour response can be obtained. The combination of multiple cytokines, in the MSC vehicle, leads to unique local expression and secretion of the immune-stimulating factors that leads to a local anti-tumour response, comprising multiple arms of the immune response, without inducing systemic toxicity as is often observed when systemically applying cytokines in tumour patients.

Furthermore, the unique properties of MSCs, which home to and engraft into tumour tissue, leads to maintained expression of the therapeutic cytokine factors in order to maintain the immune response for therapeutic effect. In one embodiment the use of an inducible promoter, preferably expressed in proximity to or within tumour tissue, or in inflamed tissue, enables local and tumour-specific cytokine expression which is subsequently reduced after the tumour (and therefore preferably the inflammation) in that region) is subsequently reduced.

The present invention also relates to a genetically modified mesenchymal stem cell (MSC), wherein said MSCs comprise one or more exogenous nucleic acid molecule(s), wherein said exogenous nucleic acid molecule(s) comprise a region encoding two or more immune response-stimulating cytokines operably linked to one or more promoters or promoter/enhancer combinations.

In a preferred embodiment the genetically modified mesenchymal stem cell as described herein is characterised in that the exogenous nucleic acid comprises a region encoding two or more immune response-stimulating cytokines operably linked to one or more promoters or promoter/enhancer combinations, wherein the cytokines are selected from the group consisting of IL-2, IL-7, IL-12, IL-15, IL21, IFN gamma and IFN beta.

In a preferred embodiment the genetically modified mesenchymal stem cell as described herein is characterised in that the two or more immune response-stimulating cytokines comprise at least IL-12, and one or more of IL-2, IL-7, IL-15, and/or IL-21.

In a preferred embodiment the genetically modified mesenchymal stem cell as described herein is characterised in that the two or more immune response-stimulating cytokines comprise least IL-7 and IL-21.

In a preferred embodiment the genetically modified mesenchymal stem cell as described herein is characterised in that the two or more immune response-stimulating cytokines comprise at least one chemokine and at least one immune response-stimulating cytokine is selected from the group consisting of IL-2, IL-7, IL-12, IL-15, IL21, IFN gamma and IFN beta.

The present invention encompasses in some embodiments the combination of cytokine transgenes in the cells as described herein, in particular any given specific combination of individual cytokines or chemokines disclosed herein, preferably any given specific combination of two or more of -2, IL-7, IL-12, IL-15, IL21, IFN gamma, IFN beta, CD28, chemokine (C-C motif) ligand 1, 2, 4, 17, 19, 22, 23 (CCL1, CCL2, CCL4, CCL17, CCL19, CCL22, CCL23), stromal cell-derived factor 1 (SDF-1).

The MSCs defined by two or more immune response-stimulating cytokines and the method of tumour treatment comprising administration of MSCs defined by one or more immune response-stimulating cytokines in combination with other anti-tumour immunotherapies are bound by the surprising and beneficial concept of local immune system stimulation in an anti-tumour immune response, either by the innate immune system or by combined immunotherapies. It was unexpected that MSCs encoding transgenic immune-stimulating cytokines may be used as an effective anti-tumour adjuvant in stimulating an anti-tumour response. The related prior art teaches only the use of MSC vehicles for the local administration of (transgenic) cytotoxic agents, with a direct effect. However, the use of MSCs encoding (potentially multiple) transgenic immune-stimulatory cytokines, or the combination of such MSCs with anti-tumour immunotherapies, to boost the local anti-tumour immune response, represent special technical features of the invention.

Surprisingly, the MSCs modified with multiple cytokines as described herein show unexpectedly good expression and secretion of said cytokines both in vitro and in vivo. A skilled person would not expect that these particular cytokines could be expressed in sufficient quantities and exported from the cells in sufficient quantities to induce or enhance the desired local immune response, based on either the innate response or and immunotherapy.

The invention therefore relates to a genetically modified mesenchymal stem cell described herein comprising one or more exogenous nucleic acid molecule(s), wherein said exogenous nucleic acid molecule(s) comprise a region encoding two or more immune response-stimulating cytokines for use as a medicament in the treatment of a tumour. Any of the features disclosed herein with respect to the method of treatment or medical administration or application of the MSCs, or their combined administration with an anti-tumour immunotherapy described herein, also apply to the MSCs comprising transgenic material for at least two or more immune response-stimulating cytokines.

The invention provides suitable means for local stimulation of an immune response directed against tumour tissue in a subject. This includes the natural immune response of the patient and immunotherapeutic treatments aiming to direct the immune response against the tumour (e.g. checkpoint inhibitors, CARTs against tumour antigens and other tumour immunotherapies). Such support or induction of the immune response may in various clinical settings be beneficial in order to initiate and maintain the immune response and evade the tumour-mediated immunosuppression that often blocks this activation.

The cells of the present invention may be used to enhance the activities and/or increase amounts of endogenous immune cells that are already present in the subject. Alternatively or additionally, additional immune cells (either autologous or allogeneic) may be administered in combination with the MSCs (for example concurrently or sequentially) of the invention in order to enhance the desired therapeutic immune response.

The construction of the genetically modified MSCs described herein may be carried out using techniques known to a person skilled in the art.

In one embodiment, the genetically modified mesenchymal stem cell as described herein is characterised in that the exogenous nucleic acid comprises viral vector sequences, for example in the form of a viral expression construct.

In one embodiment, the genetically modified mesenchymal stem cell as described herein is characterised in that the exogenous nucleic acid is a non-viral expression construct.

As used herein, "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" or "natural" genome. Exogenous nucleic acids may be integrated or non-integrated in the genetic material of the target mesenchymal stem cell, or relate to stably transduced nucleic acids.

Any given gene delivery method is encompassed by the invention and preferably relates to viral or non-viral vectors, as well as biological or chemical methods of transfection, or combinations thereof. The methods can yield either stable or transient gene expression in the system used.

Genetically modified viruses have been widely applied for the delivery of genes into stem cells. Adenoviruses may be applied, or RNA viruses such as Lentiviruses, or other retroviruses. Adenoviruses have been used to generate a series of vectors for gene transfer in the field of gene therapy and cellular engineering. The initial generation of adenovirus vectors were produced by deleting the EI gene (required for viral replication) generating a vector with a 4 kb cloning capacity. An additional deletion of E3 (responsible for host immune response) allowed an 8 kb cloning capacity. Further generations have been produced encompassing E2 and/or E4 deletions. The use of any given adenovirus vector, for example those according to those described above, is encompassed by the present invention.

Lentiviruses are members of Retroviridae family of viruses (M. Scherr et al., Gene transfer into hematopoietic stem cells using lentiviral vectors. Curr Gene Ther. 2002 February; 2(1):45-55). Lentivirus vectors are generated by deletion of the entire viral sequence with the exception of the LTRs and cis acting packaging signals. The resultant vectors have a cloning capacity of about 8 kb. One distinguishing feature of these vectors from retroviral vectors is their ability to transduce dividing and non-dividing cells as well as terminally differentiated cells.

Non-viral methods may also be employed, such as alternative strategies that include conventional plasmid transfer and the application of targeted gene integration through the use of nuclease-based gene editing, integrase or transposase technologies. These represent approaches for vector transformation that have the advantage of being both efficient, and often site-specific in their integration. Physical methods to introduce vectors into cells are known to a skilled person. One example relates to electroporation, which relies on the use of brief, high voltage electric pulses which create transient pores in the membrane by overcoming its capacitance. One advantage of this method is that it can be utilized for both stable and transient gene expression in most cell types. Alternative methods relate to the use of liposomes or protein transduction domains. Appropriate methods are known to a skilled person and are not intended as limiting embodiments of the present invention.

The invention encompasses the use of more than one virus, or a virus and other gene editing event or genetic modification, including the use of or mRNA, siRNA, miRNA, or other genetic modification in order to manipulate gene expression any given relevant factor. The immune response-stimulating cytokine may, in some embodiments of the present invention, relate to multiple cytokines and/or chemokines or combinations thereof.

In one embodiment the genetically modified mesenchymal stem cell as described herein is characterised in that the promoter or promoter/enhancer combination yields constitutive expression of the exogenous nucleic acid. Due to the beneficial homing properties of MSCs to tumours within the body of a subject post systemic administration or after local administration, the use of a constitutive promoter for expression of the one or more immune response-stimulating cytokine(s) is preferred.

In one embodiment the genetically modified mesenchymal stem cell as described herein is characterised in that the promoter is an EF1 alpha promoter, for example the EF1 alphaS promoter.

In one embodiment the genetically modified mesenchymal stem cell as described herein is characterised in that the promoter is the PGK promoter.

In one embodiment the genetically modified mesenchymal stem cell as described herein is characterised in that the promoter is the CMV or SV40 viral promoters.

In one embodiment the genetically modified mesenchymal stem cell as described herein is characterised in that the promoter is the GAG promoter.

In one embodiment the genetically modified mesenchymal stem cell as described herein is characterised in that the promoter is the UBC promoter.

In one embodiment, the genetically modified mesenchymal stem cell as described herein is characterised in that the immune response-stimulating cytokine is expressed when the genetically modified mesenchymal stem cell comes into proximity with tumour tissue or tumour stromal tissue.

Given that mesenchymal stem cells can show a selective migration to different tissue microenvironments in normal as well as diseased settings, the use of tissue-specific promoters, or other promoters linked to a particular disease microenvironment, or promoters induced by a differentiation pathway initiated in the recruited stem cell, is encompassed in the present invention and can be used to drive the selective expression of therapeutic genes, such as the cytokines described herein, specifically within a defined biological context.

In a preferred embodiment, the genetically modified mesenchymal stem cell as described herein is characterized in that the promoter or promoter/enhancer combination is induced upon differentiation of said cell post-administration. One example of differentiation post-administration is endothelial differentiation, wherein the MSC can engraft and subsequently differentiate into an endothelial or endothelial-like cell in or in proximity to the tumour tissue, thereby enabling expression of the stimulatory cytokine in a local manner.

Stem cells that are recruited to other tissue niches, but do not experience the disease region (the tumour environment), should not express the therapeutic gene. This approach allows a significant degree of potential control for the selective expression of the therapeutic gene within a defined microenvironment, thereby reducing the probability of the occurrence of known toxicities associated with systemic administration of pro-inflammatory cytokines, and has been successfully applied to regulate therapeutic gene expression during neovascularization. Potential approaches to such gene modifications are disclosed in WO 2008/150368 and WO 2010/119039, which are hereby incorporated in their entirety.

In one embodiment, the genetically modified mesenchymal stem cell as described herein is characterised in that the promoter is the Tie2 promoter.

Promoters can be introduced that are selectively regulated in the context of inflammation or neovascularization. In this regard the Tie2-promoter, FlkI promoter and intronic enhancer, endothelin-1 promoter and the pre-proendothelin-1 promoter have been studied for endothelial specific expression (Huss, R, von Luttichau, I, Lechner, S, Notohamiprodjo, M, Seliger, C, Nelson, P (2004) [Chemokine directed homing of transplanted adult stem cells in wound healing and tissue regeneration]. Verh Dtsch Ges Pathol 88:170-173).

Another embodiment of the invention provides mesenchymal stem cells that comprise a promoter or promoter/enhancer combination, which is inducible by inflammatory mediators and which controls the transcription of the stimulatory cytokine (immune response-stimulating cytokine). These inflammatory mediators can be released by the tumour's stromal tissue so that the expression of the cytotoxic protein in the mesenchymal stem cells is induced when the stem cells come into proximity with the tumour's stromal tissue. The inflammatory mediators can for example be cytokines, such as TNF alpha or IFN gamma. In particular the promoter can be the RANTES promoter, which can inter alia be induced by TNFOC or IFN gamma (Nelson P J, Kim H T, Manning W C, et al. Genomic organization and transcriptional regulation of the RANTES chemokine gene. J Immunol 1993; 151 (5): 2601-12; von Luettichau I, Nelson P J, Pattison J M, et al. RANTES chemokine expression in diseased and normal human tissues. Cytokine 1996; 8(1):89-98; Nelson P J, Pattison J M, Krensky A M. Gene expression of RANTES. Methods Enzymol 1997; 287:148-62; Duell E J, Casella D P, Burk R D, et al. Inflammation, genetic polymorphisms in proinflammatory genes TNF-A, RANTES, and CCR5, and risk of pancreatic adenocarcinoma. Cancer Epidemiol Biomarkers Prev 2006; 15 (4):726-31; Marfaing-Koka, A., et al., Regulation of the production of the RANTES chemokine by endothelial cells. Synergistic induction by IFN-gamma plus TNF-alpha and inhibition by IL-4 and IL-13. Journal of Immunology, 1995. 154(4): p. 1870-8).

In one embodiment, the genetically modified mesenchymal stem cell as described herein is characterised in that the promoter is the RANTES promoter. The "RANTES" promoter is also known in the art as the "CCL5" promoter.

Further examples of promoters, which are inducible by pro-inflammation mediators are the NF-kB-responsive element and in general promoters, which can be induced by TNF.

Additionally, promoters activated by anti-inflammatory mediators (e.g. TGF-beta) can be used to achieve a targeted expression the cytotoxic protein in the mesenchymal stem cells. Examples are promoters which contain Smad-binding elements. Using promoters, which are inducible by inflammation mediators, enables a selective treatment of tumours, which have not yet undergone angiogenesis.

Additionally, promoters activated in cancerous tissue, or activated by signals released by cancerous cells, can be used in the present invention to achieve selective expression of the encoded cytokine in the relevant location within the patient in order to avoid unwanted systemic effects. One example of a promoter that is up-regulated in cancers is the HSP70 promoter. The HSP70 protein, which is the major stress-inducible heat shock protein, is a chaperone protein abundantly and preferentially expressed in human tumours and tumour cell lines. Owing to the ability of Hsp70 to protect cells from a wide range of apoptotic and necrotic stimuli, it has been assumed that Hsp70 may confer survival advantage to tumour cells (Rohde et al., Genes Dev. Mar. 1, 2005; 19(5): 570-582, Nylandsted et al., Ann N Y Acad Sci. 2000; 926:122-5, Ramp et al., Histol Histopathol. 2007 October; 22(10):1099-107, Ricaniadis et al., Eur J Surg Oncol. 2001 February; 27(1):88-93). The HSP70 promoter is therefore one option for selective expression of the therapeutic cytokine encompassed by the present invention. Further information on the HSP70 promoter can be obtained from Wu et al., Proc. Natl. Acad. Sci. USA, Vol. 83, pp. 629-633, 1986.

The use of a "tumour-specific" promoter, or promoter preferentially expressed or induced under inflammatory or "cancer-like" conditions, may show a synergistic effect in combination with the MSC homing properties with respect to reduction of unwanted systemic effect. The MSCs of the present invention migrate towards inflammatory, in particular tumour, tissue, thereby providing effective means for avoiding systemic expression of the encoded cytokine in the body of a patient. The use of a promoter for the expression of the cytokine that is preferentially expressed under conditions of inflammation or of being present in tumour tissue further enhances the reduction in systemic expression in a synergistic manner, thereby providing surprising benefits in the MSC-based mode of administration of the cytokines described herein.

In one embodiment the genetically modified mesenchymal stem cell as described herein is characterised in that the immune response-stimulating cytokine maintains or enhances the activity, survival and/or number of immune cells within or in proximity to tumour tissue.

As known in the art, an immune response-stimulating cytokine is to be understood as any cytokine that leads to or produces either directly or indirectly the induction, activation and/or enhancement of an immune response, preferably directed against an antigen, for example a tumour antigen. In particular, the immune response-stimulating cytokines of the invention are preferably considered as cytokines that leads to the induction, activation and/or enhancement of an immune response beneficial for the treatment of a tumour disease.

As used herein, the terms immune response-modulating cytokine or immune response-associated cytokine may be used interchangeably and relate to molecules that participate, modulate, control and/or regulate the immune response and/or inflammatory reactions including anti-tumour activity due to the differentiation, maturation and activation of immune cells.

Cytokines are a diverse group of non-antibody proteins that act as mediators between cells. Cytokines are currently being clinically used as biological response modifiers for the treatment of various disorders. The term cytokine is a general term used to describe a large group of proteins.

Particular kinds of cytokines may include Monokines, namely cytokines produced by mononuclear phagocytic cells, Lymphokines, namely cytokines produced by activated lymphocytes, especially Th cells, Interleukins, namely cytokines that act as mediators between leukocytes and Chemokines, namely small cytokines primarily responsible for leucocyte migration. Cytokine signaling is flexible and can induce both protective and damaging responses. They can produce cascades, or enhance or suppress production of other cytokines. Despite the various roles of cytokines, a skilled person is aware of which cytokines may be considered as immune response-stimulating and therefore applied in the treatment of a tumour disease as described herein.

Cytokines have the ability to modulate immune responses and are often utilised by a tumour to allow it to grow and manipulate the immune response. These immune-modulating effects allow them to be used as drugs to provoke an immune response against the tumour.

The following cytokines may be referred to as immune-response stimulatory or immune response-modulatory cytokines.

Two commonly used groups of cytokines in anti-tumour therapy are the interferons and interleukins.

Interferons are cytokines produced by the immune system usually involved in an anti-viral response, but also show effectiveness in the treatment of cancer. There are three groups of interferons (IFNs): type I (IFN alpha and IFN beta), type 2 (IFN gamma) and the relatively newly discovered type III (IFN lambda). IFN alpha has been applied in the treatment of hairy-cell leukaemia, AIDS-related Kaposi's sarcoma, follicular lymphoma, chronic myeloid leukaemia and melanoma. Type I and II IFNs have been researched extensively and although both types promote the anti-tumour effects of the immune system, only type I IFNs have been shown to be clinically effective in cancer treatment so far. IFN lambda has been tested for its anti-tumour effects in animal models, and shows promise.

In a preferred embodiment the genetically modified mesenchymal stem cell as described herein is characterised in that the immune response-stimulating cytokine is IFN alpha.

In a preferred embodiment the genetically modified mesenchymal stem cell as described herein is characterised in that the immune response-stimulating cytokine is IFN gamma.

In a preferred embodiment the genetically modified mesenchymal stem cell as described herein is characterised in that the immune response-stimulating cytokine is IFN beta.

According to some embodiments of the present invention, the immune-response stimulatory or immune response-modulatory cytokines are preferably those involved in T cell regulation or with effector function for T cells (T cell regulatory cytokines). These cytokines exhibit desired properties with respect to inducing a pro-inflammatory microenvironment and thereby facilitating the activation of the immune system against the tumour and/or enhance the efficacy of anti-tumour immunotherapeutic treatments. Such cytokines may be able to attract immune effector cells, such as T cells, and promote the maturation of memory immune cells. Examples of these cytokines are IFN gamma, IL-2, IL-12, IL-23, IL-15 and IL-21 (refer Kelley's Textbook of Rheumatology; Firestein et al, 8th ed. (ISBN 978-1-4160-3285-4), p 367 "Cytokines").

The specific molecules mentioned herein relate preferably to mammalian molecules, preferably human molecules, for reasons of suitability for administration in human subjects. For example, the cytokines and/or chemokines mentioned herein relate preferably to the human sequences, as can be obtained by a skilled person without undue effort, for example from a sequence database such as those maintained by the National Center for Biotechnology Information (NCBI).

Protein sequences or protein-coding nucleic acid sequences may be modified in comparison to commonly known sequences, for example by making e. g. conservative amino acid substitutions in a protein sequence, or by using the degeneracy of the genetic code in order to change the coding sequence without changing the encoded protein sequence. As a skilled person is aware, the sequences of biological molecules can be changed (mutated) via standard techniques, their properties thereby being improved or maintained in comparison to the known original sequence. Any modified cytokine sequence that maintains the basic properties of, or is functionally analogous to, the known sequence is therefore encompassed in the scope of the present invention.

In a preferred embodiment the genetically modified mesenchymal stem cell as described herein is characterised in that the immune response-stimulating cytokine is IL-2.

Interleukin-2 is an example of a cytokine that can enhance the anti-tumour activity of the immune system and thus can be used as a treatment in cancer. Interleukin-2 has been used for the treatment of malignant melanoma (trade name, Proleukin) and renal cell carcinoma. In normal physiology it promotes both effector T cells (cells that produce the immune response) and T-regulatory cells (cells that repress the immune response), but its exact mechanism in the treatment of cancer is unknown. Recent work indicates a beneficial effect of IL-2 expression in cancer treatment. IL-2 has been used in conjunction with adoptive immunotherapies, such as CART therapies, in order to promote T-cell activation. However, systemic administration of IL-2 carries the risk of broad immune activation which contributes to the toxicities associated with CART therapies.

In a preferred embodiment the genetically modified mesenchymal stem cell as described herein is characterised in that the immune response-stimulating cytokine is IL-7.

Interleukin 7 (IL-7) is a hematopoietic growth factor secreted by stromal cells in the bone marrow and thymus. IL-7 stimulates the differentiation of multipotent (pluripotent) hematopoietic stem cells into lymphoid progenitor cells. IL-7 as an immunotherapy agent has been examined in pre-clinical animal studies and more recently in human clinical trials for various malignancies and during HIV infection (Fry T J, Mackall C L (June 2002). "Interleukin-7: from bench to clinic". Blood 99 (11): 3892-904).

In a preferred embodiment the genetically modified mesenchymal stem cell as described herein is characterised in that the immune response-stimulating cytokine is IL-15.

Interleukin 15 (IL-15) is a cytokine with structural similarity to IL-2. Like IL-2, IL-15 binds to and signals through a complex composed of IL-2/IL-15 receptor beta chain (CD122) and the common gamma chain (gamma-C, CD132). IL-15 induces cell proliferation of natural killer cells; cells of the innate immune system whose principal role is to kill virally infected or cancerous cells. IL-15 has been shown to enhance the anti-tumour immunity of CD8+ T cells in pre-clinical models (Klebanoff C A, et al. Proc. Natl. Acad. Sci. U.S.A. 101 (7): 1969-74).

In a preferred embodiment the genetically modified mesenchymal stem cell as described herein is characterised in that the immune response-stimulating cytokine is IL-21.

Interleukin-21 (IL-21) is a cytokine that has potent regulatory effects on cells of the immune system, including natural killer (NK) cells and cytotoxic T cells that can destroy virally infected or cancerous cells. IL-21 has been approved for Phase 1 and 2 clinical trials in metastatic melanoma (MM) and renal cell carcinoma (RCC) patients (Søndergaard H, Skak K, Tissue Antigens 74 (6): 467-79). It has been shown to be safe for administration with flu-like symptoms as side effects. Dose-limiting toxicities included low lymphocyte, neutrophil, and thrombocyte count as well as hepatotoxicity.

Interleukin 12 (IL-12) is an interleukin that is naturally produced by dendritic cells, macrophages and human B-lymphoblastoid cells (NC-37) in response to antigenic stimulation. IL-12 is involved in the differentiation of naive T cells into Th1 cells. It is known as a T cell-stimulating factor, which can stimulate the growth and function of T cells, thereby falling under the concept of the present invention. IL-12 is known to stimulate the production of interferon-gamma (IFN-γ) and tumour necrosis factor-alpha (TNF-α) from T cells and natural killer (NK) cells, and reduces IL-4 mediated suppression of IFN-γ. IL-12 also has a known anti-angiogenic activity. IL-12 functions by increasing production of IFN gamma, which in turn increases the production of the chemokine CXCL10.

Interleukin-12 (IL-12) plays a role in the interaction between the innate and adaptive arms of immunity by regulating inflammatory responses, innate resistance to infection, and adaptive immunity, in particular with respect to immune responses against cancer cells (Colombo et al., Cytokine Growth Factor Rev. 2002 April; 13(2):155-68). IL-12 is required for resistance to many pathogens and to transplantable or chemically induced tumours. It is known that recombinant IL-12 treatment shows anti-tumour effect on transplantable tumours, on chemically induced tumours, and in tumours arising spontaneously in genetically modified mice. Because of this ability, IL-12 has a potent adjuvant activity in cancer.

However, until the present time, excessive clinical toxicity and modest clinical response has been observed in clinical trials, thereby necessitating novel approaches and administration regimes that minimize toxicity without affecting the anti-tumour effect of IL-12. IL-12 has not been shown to have substantial activity in the tumours tested to this date via systemic administration in doses that are non-toxic to the subject.

The present invention therefore relates to the MSCs as described herein and medical use thereof, wherein the exogenous nucleic acid encodes IL-12. The MSC-based approach towards site-specific expression of IL-12 represents a novel and advantageous approach towards avoiding the toxicity inherent in IL-12 systemic administration.

The present invention enables a surprising and advantageous anti-tumour effect via the expression of an immune stimulatory cytokine in the MSCs as described herein. The expression of a stimulatory cytokine as described herein by the MSCs supports an anti-tumour immune response and leads to reduction in tumour size and/or growth, and shows a distinct reduction in and/or avoidance of the side effects produced by systemic administration of such cytokines known in the art. Side effects such as nausea and vomiting, sores in the mouth or on the lips, diarrhoea, drowsiness, allergic reactions, fever or chills, hives, itching, headache, coughing, shortness of breath, or swelling of the face, tongue, or throat, may be avoided by the MSC-based therapy described herein.

The present invention therefore provides means for reducing the side effects of cytokine therapy, and the concomitant use of cytokines with immunotherapies, by enabling local (or locally confined) tumour-specific effects, achieved preferably by systemic administration of the cells, but exerted in a tissue specific manner via cell therapy using MSCs that comprise and express said cytokines under the appropriate tissue-specific conditions.

The present invention therefore relates to a genetically modified mesenchymal stem cell for use as a medicament as described herein, wherein the exogenous nucleic acid comprises a region encoding two or more immune response-stimulating cytokines operably linked to one or more promoters or promoter/enhancer combinations, wherein the cytokines are selected from the group consisting of IL-2, IL-7, IL-12, IL-15, IL21, IFN gamma and IFN beta.

The present invention therefore relates to a genetically modified mesenchymal stem cell for use as a medicament as described herein, wherein the exogenous nucleic acid comprises a region encoding two or more immune response-stimulating cytokines operably linked to one or more promoters or promoter/enhancer combinations, wherein said cytokines comprise at least IL-7 and IL-21, IL-12 and IL-2, IL-15 and IL-12, IL-7 and IL-12, or IL-21 and IL-12.

The invention also relates to a genetically modified mesenchymal stem cell comprising an exogenous nucleic acid molecule, wherein said exogenous nucleic acid molecule comprises a region encoding an immune stimulatory molecule(s) that induce T-cell proliferation and/or differentiation (and/or maturation to a memory cell and avoidance of tumour-mediated immunosuppression) operably linked to a promoter or promoter/enhancer combination.

The immune stimulatory molecule that induces T-cell proliferation and/or differentiation may be a cytokine as described herein or another immune stimulatory molecule, such as a chemokine or combination of cytokines and chemokines. A combination may be preferred to ensure that immune cells are attracted appropriately by chemokines, activated appropriately (by the appropriate cytokine leading to activation) and are directed toward a memory phenotype (by an appropriate cytokine promoting the maturation of memory effector immune cells).

In a preferred embodiment the genetically modified mesenchymal stem cell is characterised in that the immune stimulatory molecule that induces T-cell proliferation and/or differentiation is CD28. CD28 (Cluster of Differentiation 28) is one of the proteins expressed on T cells that provide co-stimulatory signals, which are required for their activation. CD28 has also been found to stimulate eosinophil granulocytes, where its ligation with anti-CD28 leads to the release of IL-2, IL4, IL-13 and IFN gamma.

In a preferred embodiment the genetically modified mesenchymal stem cell is characterised in that the immune response-stimulating cytokine is a chemokine.

The invention also relates to genetically modified mesenchymal stem cells for use as a medicament as described herein, wherein the exogenous nucleic acid comprises a region encoding two or more immune response-stimulating cytokines operably linked to one or more promoters or promoter/enhancer combinations, wherein at least one immune response-stimulating cytokine is a chemokine.

The invention also relates to genetically modified mesenchymal stem cells for use as a medicament as described herein, wherein the exogenous nucleic acid comprises a region encoding two or more immune response-stimulating cytokines operably linked to one or more promoters or promoter/enhancer combinations, wherein at least one immune response-stimulating cytokine is a chemokine and at least one immune response-stimulating cytokine is selected from the group consisting of IL-2, IL-7, IL-12, IL-15, IL21, IFN gamma and IFN beta.

In one embodiment the genetically modified mesenchymal stem cell is characterised in that the immune response-stimulating cytokine is an inflammatory chemokine.

In one embodiment the genetically modified mesenchymal stem cell is characterised in that the immune response-stimulating cytokine is a chemokine with chemotactic properties for attracting T cells, for example, CCL1, CCL2 and/or CCL17.

Chemokines refer to a sub-group of cytokines (signalling proteins) secreted by cells. Cytokines have the ability to induce directed chemotaxis in nearby responsive cells; they are chemotactic cytokines. Proteins are classified as chemokines according to shared structural characteristics such as small size (typically approximately 8-10 kilodaltons in size), and the presence of four cysteine residues in conserved locations that are key to forming their 3-dimensional shape. Cytokines may be known under alternative definitions, such as the SIS family of cytokines, SIG family of cytokines, SCY family of cytokines, Platelet factor-4 superfamily or intercrines. Chemokines have been classified into four main subfamilies: CXC, CC, CX3C and XC. All of these proteins exert their biological effects by interacting with G protein-linked transmembrane receptors called chemokine receptors, which are selectively found on the surfaces of their target cells.

The major role of chemokines is to act as chemoattractants to induce or direct migration of immune cells. Cells that are attracted by chemokines follow a signal of increasing chemokine concentration towards the source of the chemokine. Some chemokines control cells of the immune system during processes of immune surveillance, such as directing lymphocytes to the lymph nodes so they can screen for invasion of pathogens by interacting with antigen-presenting cells residing in these tissues. Some chemokines have roles in development; they promote angiogenesis (the growth of new blood vessels), or guide cells to tissues that provide specific signals critical for cellular maturation. Other chemokines are inflammatory and are released from a wide variety of cells in response to bacterial infection, viruses and agents that cause physical damage such as silica or the urate crystals that occur in gout. Their release is often stimulated by pro-inflammatory cytokines such as interleukin 1. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing.

Chemokines are generally considered pro-inflammatory or homeostatic. Pro-inflammatory cytokines can be induced during an immune response to recruit cells of the immune system to a site of infection, or other immune target, such as a tumour, whereas the homeostatic cytokines are involved in controlling the migration of cells during processes of tissue maintenance or development. Inflammatory cytokines and chemokines are typically formed under pathological conditions (on pro-inflammatory stimuli, such as IL-1, TNF-alpha, LPS, or viruses) and actively participate in the inflammatory response attracting immune cells to the site of inflammation.

The invention therefore relates to the mesenchymal stem cells described herein, wherein the exogenous nucleic acid encodes an inflammatory chemokine. Such chemokines are known to a skilled person. Examples of inflammatory chemokines relate to CXCL-8, CCL2, CCL3, CCL4, CCL5, CCL11 and CXCL10, CXCL1, CXCL2.

In one embodiment of the invention, the chemokine is capable of inducing migration of T cells (T-lymphocytes) to the site of the chemokine expressing MSC. Examples of chemokines are involved in the recruitment of T lymphocytes to the site of inflammation are CCL2, CCL1, CCL22 and CCL17. These chemokines are known attractants of T-cells and can therefore be used to attract endogenous patient T-cells, or to enhance the homing of adoptive immunotherapeutics (e.g. CARTs) to the tumour. Homing of adoptive immunotherapeutics in tumours is a known deficit of many such treatments and this invention therefore carries the potential to significantly enhance the homing and subsequent therapeutic efficacy of adoptive immunotherapies, such as CARTs.

In some embodiments the chemokine is a CXC chemokine, preferably CXCL13.

CXC chemokines relate to chemokines in which the two N-terminal cysteines of CXC chemokines (or α-chemokines) are separated by one amino acid, represented in this name with an "X". There are typically two categories of CXC chemokines, those with a glutamic acid-leucine-arginine motif (ELR motif) immediately before the first cysteine of the CXC motif (ELR-positive), and those without an ELR motif (ELR-negative). An example of an ELR-positive CXC chemokine is interleukin-8 (IL-8), which induces neutrophils to leave the bloodstream and enter into the surrounding tissue. An example of an ELR-negative chemokine is CXCL13, which shows chemoattractant properties for lymphocytes.

In one embodiment of the invention the chemokine is CX3CL1, which belongs to the group of chemokines termed CX3C chemokines. The CX3C chemokines relate to chemokines that have three amino acids between the two cysteines. CX3CL1 is both secreted and tethered to the surface of the cell that expresses it, thereby serving as both a chemoattractant and as an adhesion molecule.

In some embodiments of the invention, the chemokine is selected from the group consisting of stromal cell-derived factor 1 (SDF-1; CXCL12), Chemokine (C-C motif) ligand 23 (CCL23; Macrophage inflammatory protein 3 (MIP-3)), Chemokine (C-C motif) ligand 19 (CCL19; EBI1; ELC or macrophage inflammatory protein-3-beta (MIP-3-beta)) and Chemokine (C-C motif) ligand 4 (CCL4; Macrophage inflammatory protein-1β (MIP-1β)).

The stromal cell-derived factor 1 (SDF-1) is also known as C-X-C motif chemokine 12 (CXCL12). Stromal cell-derived factors 1-alpha and 1-beta are small cytokines that belong to the chemokine family, members of which activate leukocytes and are often induced by pro-inflammatory stimuli such as lipopolysaccharide, TNF, or IL1. The chemokines are characterized by the presence of 4 conserved cysteines that form 2 disulfide bonds. They can be classified into 2 subfamilies. In the CC subfamily, the cysteine residues are adjacent to each other. In the CXC subfamily, they are separated by an intervening amino acid. The SDF1 proteins belong to the latter group. SDF-1 is produced in two forms, SDF-1α/CXCL12a and SDF-1β/CXCL12b, by alternate splicing of the same gene. The invention therefore relates to the MSCs as described herein, wherein the exogenous nucleic molecule encodes an SDF-1 chemokine, such as SDF-1α/CXCL12a and/or SDF-1β/CXCL12b.

Chemokine (C-C motif) ligand 23 (CCL23) is a cytokine belonging to the CC chemokine family that is also known as Macrophage inflammatory protein 3 (MIP-3) and Myeloid progenitor inhibitory factor 1 (MPIF-1). CCL23 is predominantly expressed in lung and liver tissue, but is also found in bone marrow and placenta. CCL23 is chemotactic for resting T cells and monocytes.

Chemokine (C-C motif) ligand 19 (CCL19) is a cytokine belonging to the CC chemokine family that is also known as EBI1 ligand chemokine (ELC) and macrophage inflammatory protein-3-beta (MIP-3-beta). CCL19 is expressed abundantly in thymus and lymph nodes, with moderate levels in trachea and colon and low levels in stomach, small intestine, lung, kidney and spleen. CCL19 is known to play an important role in trafficking of T cells in thymus, and in T cell and B cell migration to secondary lymphoid organs.

CCL4, also known as Macrophage inflammatory protein-1β (MIP-1β) is a CC chemokine with specificity for CCR5 receptors. It is a chemoattractant for natural killer cells, monocytes and a variety of other immune cells.

All immunotherapies rely on the local and timely activation of the immune response and this, in turn, relies largely on the presence of effector cells to exert their function. In the case of oncology, this function results in the killing of tumour cells. In many cases, however, only insufficient amounts of immune effector cells are attracted to the tumour and the effect of the immunotherapy is curtailed.

The chemokines described herein are capable of exhibiting T cell recruiting properties that are beneficial in an immune response against a tumour disease. The use of such chemokine molecules in the context of MSC-based expression and delivery of the molecules enables surprising benefits with respect to site-specific T cell recruitment and reduction in side effects associated non-target effects caused by systemic administration of such cytokines/chemokines.

In another aspect of the invention the use of the genetically modified mesenchymal stem cells as a medicament as described herein is characterised in that said treatment comprises the combined administration of said mesenchymal stem cell with a checkpoint inhibitor.

Normally, cells that are potentially cancerous are destroyed by the immune system. All cancer cells undergo changes that differentiate them from their neighbours, the most obvious change being the ability to multiply without inhibition. Cancer cells utilise mechanisms that avoid regular immune system control. Checkpoint proteins have been shown to function by communicating to the immune system that a potentially cancerous cell is not to be destroyed. There may be other molecules signalling that the cell is cancerous, but if there are enough checkpoint proteins on the cell surface, the immune system may overlook cancerous signals.

A ligand-receptor interaction that has been investigated as a target for cancer treatment is the interaction between the transmembrane programmed cell death 1 protein (PD-1; also known as CD279) and its ligand, PD-1 ligand 1 (PD-L1). In normal physiology PD-L1 on the surface of a cell binds to PD1 on the surface of an immune cell, which inhibits the activity of the immune cell. It appears that up-regulation of PD-L1 on the cancer cell surface may allow them to evade the host immune system by inhibiting T cells that might otherwise attack the tumour cell. Antibodies that bind to either PD-1 or PD-L1 and therefore block the interaction may allow the T-cells to attack the tumour.

Checkpoint inhibitors (also known as immune checkpoint modulators, or CPMs) are designed to lessen the effectiveness of checkpoint proteins. They may have a variety of mechanisms of action, but if effective, they enable the immune system to recognize other molecules on the surface of the cancer cells.

In one embodiment the medical use of the genetically modified mesenchymal stem cell as described herein is characterised by the combined administration of a checkpoint inhibitor, preferably a PD-L1 and/or PD-1 inhibitor, with said MSCs. Examples include Nivolumab (BMS-936558, MDX-1106, ONO-4538), a fully human Immunoglobulin G4 (IgG4) monoclonal PD-1 antibody, Lambrolizumab (MK-3475), a humanized monoclonal IgG4 PD-1 antibody, and BMS-936559, a fully human gG4 PD-L1 antibody.

In one embodiment the medical use of the genetically modified mesenchymal stem cell as described herein is characterised by the combined administration of a checkpoint inhibitor, preferably a CTLA-4 inhibitor, with said MSCs. Examples include Tremelimumab (Pfizer, NY, USA) and ipilimumab, two fully human monoclonal antibodies against CTLA-4.

The combined administration of the MSCs expressing an immune response-stimulating cytokine and/or an immune stimulatory molecule that induces T-cell proliferation and/or differentiation together with a checkpoint inhibitor leads to a synergistic effect with respect to the desired anti-cancer effect. The cytokine or other immune stimulator provides local enhancement of the T cell response against the cancer tissue, whilst the checkpoint inhibitor also enables the T cells to more effectively attack and destroy cancerous tissue. The effects of these two agents are combined in a synergistic manner, resulting in a technical effect greater than the sum of these two aspects when considered alone.

In a further embodiment, the invention relates to the genetically modified mesenchymal stem cell for use as a medicament as described herein, wherein the immunotherapy comprises the administration of tumour antigens.

The present invention is used to enhance the therapeutic efficacy of cancer vaccines. Cancer vaccines direct the immune system to mount an attack against cancer cells in the body. Instead of preventing disease, like vaccines used to prevent infection, they activate the immune system to attack a disease that already exists. Some cancer treatment vaccines are made up of cancer cells, parts of cells, or pure antigens. Sometimes a patient's own immune cells, such as T-cells, or antigen presenting cells, are removed and exposed to these substances in the lab to create the vaccine. Once the vaccine is ready, it's injected into the body to mediate the immune response against cancer cells. Vaccines are often combined with other substances or cells called adjuvants that help boost the immune response even further. Cancer vaccines cause the immune system to attack cells with one or more specific antigens. Activation of the cellular adaptive immune response leads to immunological memory, so, it's hoped that the vaccine might continue to work long after it's given. In many cases, the efficacy and immune activation of cancer vaccines has been hindered by the tumour-mediated immunosuppression. The combined of the cancer vaccine with said mesenchymal stem cells is expected to remove or downgrade the immunosuppression, or promote immune activation in spite of any persisting immunosuppression.

The MSCs as described herein may therefore be considered a therapeutic agent themselves, or as an adjuvant for a co-administered immunotherapeutic agent or agents.

A further aspect of the invention relates to a genetically modified mesenchymal stem cell for use as a medicament as described herein, wherein said treatment comprises the combined administration of said mesenchymal stem cell with immune cells. It is encompassed within the invention that administration of genetically modified MSCs prior to immune cells (e.g. CARTs) will enhance the chemoattraction of CARTs and other immune effector cells due to the expression of appropriate chemokines. The expression of stimulating cytokines will enhance the activation of T-cells only locally, preferably within or in proximity to the tumour, and subsequently lead to a memory effector cell phenotype, thereby prolonging the therapeutic effect of the treatment.

The response to pathogens or cancerous tissue is orchestrated by complex interactions and activities of a large number of diverse cell types involved in an immune response. Immune cells as used herein may relate to any of the following cell types, as described in the context of the following processes: The innate immune response is the first line of defence and occurs soon after pathogen exposure or exposure to "foreign" or cancerous matter. It is carried out by phagocytic cells such as neutrophils and macrophages, cytotoxic natural killer (NK) cells, and granulocytes. The subsequent adaptive immune response includes antigen-specific defence mechanisms and may take days to develop. Cell types with critical roles in adaptive immunity are antigen-presenting cells including macrophages and dendritic cells. Antigen-dependent stimulation of various cell types including T cell subsets, B cells, and macrophages all play critical roles in host defense. Immune cells as described herein relate to biological cells involved in the immune response in a subject. Immune cells are preferably selected from T Cells, B Cells, Dendritic Cells, Granulocytes, Innate Lymphoid Cells (ILCs), Megakaryocytes, Monocytes/Macrophages, Natural Killer (NK) Cells, Platelets, Red Blood Cells (RBCs) and/or Thymocytes.

The subject from which the mesenchymal stem cells and/or immune cells are obtained may be the same subject, to whom the cells are intended to be administered after cultivation. Such cells may therefore be considered autologous. The cells may however be obtained from a subject distinct from the intended patient, therefore being considered allogenic. As used herein, a cell is "allogenic" with respect to a subject if it or any of its precursor cells are from another subject of the same species. As used herein, a cell is "autologous" with respect to a subject if it or its precursor cells are from the same subject. In a preferred embodiment, the immune cells are autologous to the subject of medical treatment.

In a preferred embodiment, the immune cell is a T cell. In other embodiments, the immune cell is a T cell comprising an artificial T cell receptor, such as a chimeric antigen receptor (CARTs), wherein said T cell receptor binds specifically to a tumour antigen (Lee, D W et al., Clin Cancer Res; 2012; 18(10); 2780-90). In further embodiments the immune cell is a macrophage, preferably an M1 macrophage, and/or a monocyte.

Monocytes are a type of white blood cells (leukocytes). They are the largest of all leukocytes. They are part of the innate immune system of vertebrates including all mammals (humans included). Monocytes are produced by the bone marrow from precursors called monoblasts, bipotent cells that differentiated from hematopoietic stem cells. Monocytes circulate in the bloodstream for about one to three days and then typically move into tissues throughout the body. They constitute between three to eight percent of the leukocytes in the blood. In tissues monocytes mature into different types of macrophages at different anatomical locations.

Macrophages, sometimes called macrophagocytes, are cells produced by the differentiation of monocytes in tissues. Monocytes and macrophages are phagocytes. Macrophages function in both non-specific defense (innate immunity) as well as help initiate specific defense mechanisms (adaptive immunity) of vertebrate animals. Macrophages predominantly expressing the killer phenotype are called M1 macrophages, whereas those involved in tissue repair are called M2 macrophages. The role of macrophages is to phagocytose, or engulf and then digest, cellular debris and pathogens, either as stationary or as mobile cells. They also stimulate lymphocytes and other immune cells to respond to pathogens. They are specialized phagocytic cells that attack foreign substances, infectious microbes and cancer cells through destruction and ingestion.

In one embodiment the invention therefore relates to cancer immunotherapy and approaches involving adoptive cell transfer, which encompasses T cell-based cytotoxic responses to attack cancer cells.

Cancer immunotherapy attempts to stimulate the immune system to reject and destroy tumours. Initially, immunotherapy treatments involved administration of cytokines such as Interleukin. Thereafter, due to the adverse effects of intravenously and systemically administered cytokines, alternative approaches were attempted using the extraction of lymphocytes from the blood and expanding these cells in vitro against a tumour antigen before injecting the cells with appropriate stimulatory cytokines. The cells would then specifically target and destroy the tumour expressing antigen against which they have been raised. Despite these approaches, methods for appropriate stimulation of such cells with cytokines were not sufficiently effective to produce convincing tumour-reduction. Significant side effects also arose from the large quantities of cytokine required.

One approach to these previous attempts at immunotherapy involves engineering patients' own immune cells to recognize and attack their tumours. And although this approach, called adoptive cell transfer (ACT), has been restricted to clinical trials so far, treatments using these engineered immune cells have generated therapeutic responses in patients with advanced cancer.

The present invention therefore encompasses adoptive cell transfer in combination with administration of the MSCs described herein. It is encompassed within the invention that administration of genetically modified MSCs prior to immune cells (e.g. CARTs) will enhance the chemoattraction of CARTs and other immune effector cells administered during adoptive cell transfer due to the expression of appropriate chemokines. The expression of stimulating cytokines will enhance the activation of T-cells only locally, preferably within or in proximity to the tumour, and subsequently lead to a memory effector cell phenotype, thereby prolonging the therapeutic effect of the treatment.

Adoptive cell transfer uses T cell-based cytotoxic responses to attack cancer cells. T cells that have a natural or genetically engineered reactivity to a patients cancer are generated in vitro and then transferred back into the cancer patient. Autologous tumour-infiltrating lymphocytes have been used as an effective treatment for patients with metastatic melanoma. This can be achieved by taking T cells that are found with the tumour of the patient, which are trained to attack the cancerous cells. These T cells may be referred to as tumour-infiltrating lymphocytes (TIL). Such T cells may be stimulated to multiply in vitro using high concentrations of IL-2, anti-CD3 and allo-reactive feeder cells. Traditionally, these T cells are then transferred back into the patient along with exogenous administration of IL-2 to further boost their anti-cancer activity.

The present invention encompasses in one embodiment the administration of IL-2 via the genetically modified MSC as described herein. Through this approach the side effects of systemic administration of IL-2 are avoided, whilst the beneficial effects of the T cell transfer are maintained and/or enhanced. Similar effects are obtained for IL-12, IL-7, IL-21 and/or IL-15, alone or in combinations thereof, to achieve activation and establishment of immunological memory.

The present invention therefore provides novel means for local and tissue-specific cytokine production for the stimulation of an anti-tumour immune response, mediated preferably by cytotoxic T cells and/or NK cells.

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell; with transfer of their coding sequence facilitated by retroviral vectors.

Genetically engineered T cells may, in one embodiment, be created by infecting patients cells with a virus that contain a copy of a T cell receptor (TCR) gene that is specialised to recognise tumour antigens. The virus is not able to reproduce within the cell however integrates into the human genome. This is beneficial as new the TCR gene remains stable in the T-cell. A patients own T cells are exposed to these viruses and then expanded non-specifically or stimulated using the genetically engineered TCR. The cells are then transferred back into the patient and ready to have an immune response against the tumour. Second- and third-generation CARs typically consist of a piece of monoclonal antibody, called a single-chain variable fragment (scFv), that resides on the outside of the T-cell membrane and is linked to stimulatory inside the T cell. The scFv portion guides the cell to its target antigen. Once the T cell binds to its target antigen, the stimulatory molecules provide the necessary signals for the T cell to become fully active. In this fully active state, the T cells can more effectively proliferate and can attack cancer cells.

The combined administration of the MSCs expressing an immune response-stimulating cytokine and/or an immune stimulatory molecule that induces T-cell proliferation and/or differentiation together with immune cells, preferably T cells, such as those described herein, and optionally in further combination with a checkpoint inhibitor, leads to a synergistic effect with respect to the desired anti-cancer effect. Checkpoint inhibition can be combined with the MSCs expressing stimulatory cytokines, in order to enhance the anti-tumour effect of additionally administered immune cells, thereby creating a combination of factors associated with unexpected efficacy in anti-tumour treatment.

In a further embodiment, the invention relates to the genetically modified mesenchymal stem cell for use as a medicament as described herein, wherein the immunotherapy comprises the administration of patient-derived tumour material.

In a further embodiment, the invention relates to the genetically modified mesenchymal stem cell for use as a medicament as described herein, wherein the immunotherapy comprises the administration of an antibody or antibody fragment targeted to a tumour-specific antigen.

For example, antibody-dependent cell-mediated cytotoxicity (ADCC) is a mechanism of cell-mediated immune defense whereby an effector cell of the immune system actively lyses a target cell, such as a cancer cell, whose membrane-surface antigens have been bound by specific antibodies. It is one of the mechanisms through which antibodies, as part of the humoral immune response, can act to limit and contain cancerous growth. Previous reports have indicated that ADCC is an important mechanism of action of therapeutic monoclonal antibodies, including trastuzumab and rituximab, against tumours. The combined administration of the MSC as described herein with an anti-tumour antibody treatment is encompassed by the invention.

For example, bi-specific antibodies simultaneously targeted to a tumour-specific antigen and the CD3 molecule on T-cells may be administered as the anti-tumour immunotherapy.

BRIEF DESCRIPTION OF THE DRAWINGS

The following figures are presented in order to describe particular embodiments of the invention, by demonstrating a practical implementation of the invention, without being limiting to the scope of the invention or the concepts described herein.

DETAILED DESCRIPTION

Figure 1:
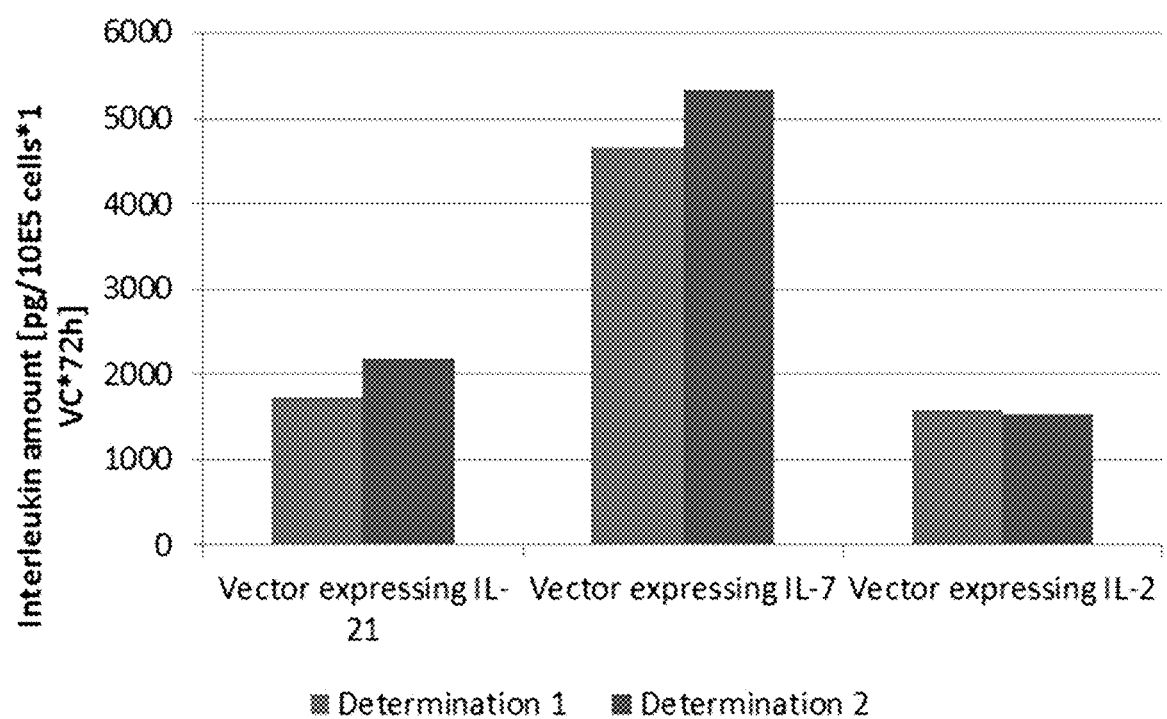
FIG. 1: Genetically modified human MSC expressing cytokines in vitro: Primary human MSC were transduced (MOI of 0.25) with retroviral vectors expressing the cytokines indicated in the graphic and the pac puromycin resistance gene. After transduction, the transduced MSC were selected using puromycin and the average vector copy number per cell was determined by qPCR. The selected cells were then seeded for ELISA-measurements (Human IL-2 Thermo ScientificEH2IL2, Human IL-7 Thermo Scientific EHIL7, Human IL-21 Thermo Scientific EHIL21). $1 \times 10^5$ cells were seeded 72 h after seeding, the supernatants were collected and tested subsequently. The generated data were normalized on 10E5 cells and one vector copy number.

An important role of the immune system is to identify and eliminate tumours. The transformed cancerous cells of tumours express antigens that are not found on normal cells. To the immune system, these antigens appear foreign, and their presence causes immune cells to attack the transformed tumour cells. The antigens expressed by tumours have several sources. Some are derived from oncogenic viruses like human papillomavirus, which causes cervical cancer, while others are the organism's own proteins that occur at low levels in normal cells but reach high levels in tumour cells. One example is an enzyme called tyrosinase that, when expressed at high levels, transforms certain skin cells (e.g. melanocytes) into tumours called melanomas. A third possible source of tumour antigens are proteins normally important for regulating cell growth and survival, that commonly mutate into cancer inducing molecules called oncogenes.

The main response of the immune system to tumours is to destroy the abnormal cells using killer T cells, sometimes with the assistance of helper T cells. Tumour antigens are presented on MHC class I molecules in a similar way to viral antigens. This allows killer T cells to recognize the tumour cell as abnormal. NK cells also kill tumorous cells in a similar way, especially if the tumour cells have fewer MHC class I molecules on their surface than normal; this is a common phenomenon with tumours. Some tumour cells also release products that inhibit the immune response; for example by secreting the cytokine TGF-β, which suppresses the activity of macrophages and lymphocytes.

The present invention therefore provides means for supporting an anti-tumour immune reaction by the expression of an immune-stimulating cytokine from the genetically modified MSCs described herein.

Immunotherapy is to be understood in the context of the present invention to encompass any therapeutic agent that uses the immune system to treat cancer. Immunotherapy exploits the fact that cancer cells have subtly different molecules on their surface that can be detected by the immune system. These molecules, known as cancer antigens, are most commonly proteins, but also include molecules such as carbohydrates. Immunotherapy provokes or enhances the immune system in attacking the tumour cells by using these antigens as targets.

Immunotherapy encompasses, without limitation, cellular and antibody therapy.

Cellular therapies typically involve the administration of immune cells isolated from the blood or from a tumour of the patient. Immune cells directed towards the tumour to be treated are activated, cultured and returned to the patient where the immune cells attack the cancer. Cell types that can be used in this way are, without limitation, natural killer cells, lymphokine-activated killer cells, cytotoxic T cells and dendritic cells. Dendritic cell therapy provokes anti-tumour responses by causing dendritic cells to present tumour antigens. Dendritic cells present antigens to lymphocytes, which activates them, priming them to kill other cells that present the antigen.

Antibodies are proteins produced by the immune system that bind to a target antigen on the cell surface. Those that bind to cancer antigens may be used to treat cancer. Cell surface receptors are common targets for antibody therapies and include for example CD20, CD274, and CD279. Once bound to a cancer antigen, antibodies can induce antibody-dependent cell-mediated cytotoxicity, activate the complement system, or prevent a receptor from interacting with its ligand, all of which can lead to cell death. Multiple antibodies are approved to treat cancer, including Alemtuzumab, Ipilimumab, Nivolumab, Ofatumumab, and Rituximab.

Antibody-dependent cell-mediated cytotoxicity (ADCC) is a mechanism of attack by the immune system that requires antibodies to bind to target cell surfaces. Antibodies are formed of a binding region (Fab) and the Fc region that can be detected by immune cells via their Fc surface receptors. Fc receptors are found on many immune system cells, including natural killer cells. When natural killer cells encounter antibody-coated cells, the latter's Fc regions interact with their Fc receptors, leading to the release of perforin and granzyme B. These two chemicals programmed cell death (apoptosis) in the tumour cell. Effective antibodies include Rituximab, Ofatumumab, and Alemtuzumab.

The complement system includes blood proteins that can cause cell death after an antibody binds to the cell surface. Generally, the system deals with foreign pathogens, but can be activated with therapeutic antibodies in cancer. The system can be triggered if the antibody is chimeric, humanized or human; as long as it contains the IgG1 Fc region. Complement can lead to cell death by activation of the membrane attack complex, known as complement-dependent cytotoxicity; enhancement of antibody-dependent cell-mediated cytotoxicity; and CR3-dependent cellular cytotoxicity. Complement-dependent cytotoxicity occurs when antibodies bind to the cancer cell surface, the C1 complex binds to these antibodies and subsequently protein pores are formed in the cancer cell membrane.

Tumour-associated antigens, or Tumour-specific antigens, may be targeted by the preferably cellular or antibody-based anti-tumour immunotherapy and include, without limitation, those antigens known to a skilled person or identifiable by a skilled person that are expressed solely or predominantly by tumour cells and may be targeted by immune therapy. As non-limiting examples, tumour associated or tumour specific antigens encompass proteins produced in tumour cells that have an abnormal structure due to mutation, such as proto-oncogenes, abnormal products of ras and p53 genes, or other proteins associated with tumour cells, such as tissue differentiation antigens, cluster of differentiation (often abbreviated as CD) cell surface molecules, mutant protein antigens, oncogenic viral antigens, cancer-testis antigens and vascular or stromal specific antigens. Glycoproteins, glycolipids, carbohydrates or growth factor receptors may also be considered tumour associated or tumour specific antigens as targets of anti-tumour immunotherapy.

The MSCs of the present invention are capable of supporting and/or enhancing the immunotherapies described herein through their unique properties derived from a combination of immune-response stimulating transgene cytokines and the MSCs inherent anti-inflammatory properties.

As used herein, "tumour" shall include, without limitation, a prostate tumour, a pancreatic tumour, a squamous cell carcinoma, a breast tumour, a melanoma, a basal cell carcinoma, a hepatocellular carcinoma, a choloangiocellular carcinoma, testicular cancer, a neuroblastoma, a glioma or a malignant astrocytic tumour such as glioblastma multiforme, a colorectal tumour, an endometrial carcinoma, a lung carcinoma, an ovarian tumour, a cervical tumour, an osteosarcoma, a rhabdo/leiomyosarcoma, a synovial sarcoma, an angiosarcoma, an Ewing sarcoma/PNET and a malignant lymphoma. These include primary tumours as well as metastatic tumours (both vascularized and non-vascularized).

The "mesenchymal stem cells" disclosed herein can give rise to connective tissue, bone, cartilage, and cells in the circulatory and lymphatic systems. Mesenchymal stem cells are found in the mesenchyme, the part of the embryonic mesoderm that consists of loosely packed, fusiform or stellate unspecialized cells. As used herein, mesenchymal stem cells include, without limitation, CD34-negative stem cells.

In one embodiment of the invention, the mesenchymal stem cells are plastic-adherent cells, defined in some embodiments as multipotent mesenchymal stromal cells and also include CD34-negative cells. For the avoidance of any doubt, the term mesenchymal stem cell encompasses multipotent mesenchymal stromal cells that also includes a subpopulation of mesenchymal cells, MSCs and their precursors, which subpopulation is made up of multipotent or pluripotent self-renewing cells capable of differentiation into multiple cell types in vivo.

As used herein, CD34-negative cell shall mean a cell lacking CD34, or expressing only negligible levels of CD34, on its surface. CD34-negative cells, and methods for isolating such cells, are described, for example, in Lange C. et al., "Accelerated and safe expansion of human mesenchymal stromal cells in animal serum-free medium for transplantation and regenerative medicine". J. Cell Physiol. 2007, Apr. 25.

Mesenchymal stem cells can be differentiated from hematopoietic stem cells (HSCs) by a number of indicators. For example, HSCs are known to float in culture and to not adhere to plastic surfaces. In contrast, mesenchymal stem cells adhere to plastic surfaces. The CD34-negative mesenchymal stem cells of the present invention are adherent in culture.

The genetically modified cell(s) described herein may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The present invention encompasses treatment of a patient by introducing a therapeutically effective number of cells into a subject's bloodstream. As used herein, "introducing" cells "into the subject's bloodstream" shall include, without limitation, introducing such cells into one of the subject's veins or arteries via injection. Such administering can also be performed, for example, once, a plurality of times, and/or over one or more extended periods. A single injection is preferred, but repeated injections over time (e.g., quarterly, half-yearly or yearly) may be necessary in some instances. Such administering is also preferably performed using an admixture of CD34-negative cells and a pharmaceutically acceptable carrier. Pharmaceutically acceptable carriers are well known to those skilled in the art and include, but are not limited to, 0.01-0.1 M and preferably 0.05 M phosphate buffer or 0.8% saline, as well as commonly used proprietary cryopreservation media.

Administration may also occur locally, for example by injection into an area of the subject's body in proximity to a tumour disease. MSCs have been shown to migrate towards cancerous tissue. Regardless, the local administration of the cells as described herein may lead to high levels of the cells at their site of action.

Additionally, such pharmaceutically acceptable carriers can be aqueous or non-aqueous solutions, suspensions, and emulsions, most preferably aqueous solutions. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington: The Science and Practice of Pharmacy, 20th Ed., p. 808, Lippincott Williams S-Wikins (2000). Preservatives and other additives may also be present, such as, for example, antimicrobials, antioxidants, chelating agents, inert gases, and the like.

As used herein, a "therapeutically effective number of cells" includes, without limitation, the following amounts and ranges of amounts: (i) from about $1\times10^2$ to about $1\times10^8$ cells/kg body weight; (ii) from about $1\times10^3$ to about $1\times10^7$ cells/kg body weight; (iii) from about $1\times10^4$ to about $1\times10^6$ cells/kg body weight; (iv) from about $1\times10^4$ to about $1\times10^5$ cells/kg body weight; (v) from about $1\times10^5$ to about $1\times10^6$ cells/kg body weight; (vi) from about $5\times10^4$ to about $0.5\times10^5$ cells/kg body weight; (vii) about $1\times10^3$ cells/kg body weight; (viii) about $1\times10^4$ cells/kg body weight; (ix) about $5\times10^4$ cells/kg body weight; (x) about $1\times10^5$ cells/kg body weight; (xi) about $5\times10^5$ cells/kg body weight; (xii) about $1\times10^6$ cells/kg body weight; and (xiii) about $1\times10^7$ cells/kg body weight. Human body weights envisioned include, without limitation, about 5 kg, 10 kg, 15 kg, 30 kg, 50 kg, about 60 kg; about 70 kg; about 80 kg, about 90 kg; about 100 kg, about 120 kg and about 150 kg. These numbers are based on pre-clinical animal experiments and human trials and standard protocols from the transplantation of CD34+ hematopoietic stem cells. Mononuclear cells (including CD34+ cells) usually contain between 123000 to 1:300000 CD34-negative cells.

As used herein, "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself. As used herein, ameliorating a disorder and treating a disorder are equivalent. The treatment of the present invention may also, or alternatively, relate to a prophylactic administration of said cells. Such a prophylactic administration may relate to the prevention of any given medical disorder, or the prevention of development of said disorder, whereby prevention or prophylaxis is not to be construed narrowly under all conditions as absolute prevention. Prevention or prophylaxis may also relate to a reduction of the risk of a subject developing any given medical condition, preferably in a subject at risk of said condition.

Combined administration encompasses simultaneous treatment, co-treatment or joint treatment, and includes the administration of separate formulations of MSCs with immunotherapies, such as checkpoint inhibitors and/or immune cells, whereby treatment may occur within minutes of each other, in the same hour, on the same day, in the same week or in the same month as one another. Sequential administration of any given combination of combined agents (for example MSCs, immune cells and/or checkpoint inhibitors) is also encompassed by the term "combined administration". A combination medicament, comprising one or more of said MSCs with another immunotherapeutic, such as checkpoint inhibitors and/or immune cells, may also be used in order to co-administer the various components in a single administration or dosage.

A combined immunotherapy may precede or follow treatment with genetically modified stem cells by intervals ranging from minutes to weeks. In embodiments where the other immunotherapeutic agent and genetically modified stem cells are administered separately to the site of interest, one would generally ensure that a significant period of time did not expire between the time of each delivery, such that the agent and the genetically modified stem cell would still be able to exert an advantageously combined effect on a treatment site. In such instances, it is contemplated that one would contact the cell with both modalities within about 12-24 h of each other and, more preferably, within about 6-12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

The term "stroma" as used herein refers to the supportive framework of a tissue or an organ (or gland, tissue or other structure), usually composed of extracellular matrix (ECM) and stromal cells. The stroma is distinct from the parenchyma, which consists of the key functional elements of that organ. Stromal cells (in the dermis layer) adjacent to the epidermis (the very top layer of the skin) release growth factors that promote cell division. Stroma is made up of the non-malignant host cells. Stroma provides an extracellular matrix on which tumours can grow or maintain existence or separate themselves from the immune environment.

As used herein, the term "tumour microenvironment" relates to the cellular environment in which any given tumour exists, including the tumour stroma, surrounding blood vessels, immune cells, fibroblasts, other cells, signalling molecules, and the ECM.

As used herein "cell migration" or "homing" is intended to mean movement of a cell towards a particular chemical or physical signal. Cells often migrate in response to specific external signals, including chemical signals and mechanical signals. The MSCs as described herein are capable of homing to tumour tissue or other inflammation signals.

Chemotaxis is one example of cell migration regarding response to a chemical stimulus. In vitro chemotaxis assays such as Boyden chamber assays may be used to determine whether cell migration occurs in any given cell.

For example, the cells of interest may be purified and analysed. Chemotaxis assays (for example according to Falk et al., 1980 J. Immuno. Methods 33239-247) can be performed using plates where a particular chemical signal is positioned with respect to the cells of interest and the transmigrated cells then collected and analysed. For example, Boyden chamber assays entail the use of chambers isolated by filters, used as tools for accurate determination of chemotactic behaviour. The pioneer type of these chambers was constructed by Boyden (Boyden (1962) "The chemotactic effect of mixtures of antibody and antigen on polymorphonuclear leucocytes". J Exp Med 115 (3): 453). The motile cells are placed into the upper chamber, while fluid containing the test substance is filled into the lower one. The size of the motile cells to be investigated determines the pore size of the filter; it is essential to choose a diameter which allows active transmigration. For modelling in vivo conditions, several protocols prefer coverage of filter with molecules of extracellular matrix (collagen, elastin etc.) Efficiency of the measurements can be increased by development of multiwell chambers (e.g. NeuroProbe), where 24, 96, 384 samples are evaluated in parallel. Advantage of this variant is that several parallels are assayed in identical conditions.

As used herein "engraftment" relates to the process of incorporation of grafted or transplanted tissue or cells into the body of the host. Engraftment may also relate to the integration of transplanted cells into host tissue and their survival and under some conditions differentiation into non-stem cell states.

Techniques for assessing engraftment, and thereby to some extent both migration and the bio-distribution of MSCs, can encompass either in vivo or ex vivo methods. Examples of in vivo methods include bioluminescence, whereby cells are transduced to express luciferase and can then be imaged through their metabolism of luciferin resulting in light emission; fluorescence, whereby cells are either loaded with a fluorescent dye or transduced to express a fluorescent reporter which can then be imaged; radionuclide labelling, where cells are loaded with radionuclides and localized with scintigraphy, positron emission tomography (PET) or single photon emission computed tomography (SPECT); and magnetic resonance imaging (MRI), wherein cells loaded with paramagnetic compounds (e.g., iron oxide nanoparticles) are traced with an MRI scanner. Ex vivo methods to assess biodistribution include quantitative PCR, flow cytometry, and histological methods. Histological methods include tracking fluorescently labelled cells; in situ hybridization, for example, for Y-chromosomes and for human-specific ALU sequences; and histochemical staining for species-specific or genetically introduced proteins such as bacterial β-galactosidase. These immunohistochemical methods are useful for discerning engraftment location but necessitate the excision of tissue. For further review of these methods and their application see Kean et al., MSCs: Delivery Routes and Engraftment, Cell-Targeting Strategies, and Immune Modulation, Stem Cells International, Volume 2013 (2013).

Progenitor or multipotent cells, such as the mesenchymal stem cells of the present invention, may be described as gene delivery vehicles, essentially enabling the localization and expression of therapeutic gene products in particular tissues or regions of the subject's body. Such therapeutic cells offer the potential to provide cellular therapies for diseases that are refractory to other treatments. For each type of therapeutic cell the ultimate goal is the same: the cell should express a specific repertoire of genes, preferably exogenous nucleic acids that code for therapeutic gene products, thereby modifying cell identity to express said gene product and provide a therapeutic effect, such as an immune stimulatory effect. The cells of the invention, when expanded in vitro, represent heterogeneous populations that include multiple generations of mesenchymal (stromal) cell progeny, which lack the expression of most differentiation markers like CD34. These populations may have retained a limited proliferation potential and responsiveness for terminal differentiation and maturation along mesenchymal and non-mesenchymal lineages.

As used herein "inducible expression" or "conditional expression" relates to a state, multiple states or system of gene expression, wherein the gene of interest, such as the immune stimulatory cytokine, is preferably not expressed, or in some embodiments expressed at negligible or relatively low levels, unless there is the presence of one or more molecules (an inducer) or other set of conditions in the cell that allows for gene expression. Inducible promoters may relate to either naturally occurring promoters that are expressed at a relatively higher level under particular biological conditions, or to other synthetic promoters comprising any given inducible element. Inducible promoters may refer to those induced by particular tissue- or micro-environments or combinations of biological signals present in particular tissue- or micro-environments, or to promoters induced by external factors, for example by administration of a small drug molecule or other externally applied signal.

As used herein, in "proximity with" a tissue includes, for example, within 50 mm, 10 mm, 5 mm, within 1 mm of the tissue, within 0.5 mm of the tissue and within 0.25 mm of the tissue.

The cytokines described herein may relate to any mammalian cytokine corresponding to the cytokine named herein. Preferably, the cytokines relate to the human cytokines, or mouse cytokines.

Given that stem cells can show a selective migration to different tissue microenvironments in normal as well as diseased settings, the use of tissue-specific promoters linked to the differentiation pathway initiated in the recruited stem cell is encompassed in the present invention and could in theory be used to drive the selective expression of therapeutic genes only within a defined biologic context. Stem cells that are recruited to other tissue niches, but do not undergo the same program of differentiation, should not express the therapeutic gene. This approach allows a significant degree of potential control for the selective expression of the therapeutic gene within a defined microenvironment and has been successfully applied to regulate therapeutic gene expression during neovascularization. Potential approaches to such gene modifications are disclosed in WO 2008/150368 and WO 2010/119039, which are hereby incorporated in their entirety.

EXAMPLES

The following examples are presented in order to describe practical and in some cases preferred embodiments of the invention, by demonstrating a practical implementation of the invention, without being limiting to the scope of the invention or the concepts described herein.

Experimental Models:

Mesenchymal stem cells can be extracted according to either Lange C. et al. ("Accelerated and safe expansion of human mesenchymal stromal cells in animal serum-free medium for transplantation and regenerative medicine", J. Cell Physiol. 2007, Apr. 25) or Soleimani ("A protocol for isolation and culture of mesenchymal stem cells from mouse bone marrow", Nat Protoc. 2009; 4(1):102-6).

The cells grow adherently and continuously in cell culture. MSCs may be transformed with retroviral or lentiviral vectors comprising cytokine encoding gene sequences. Viral constructs can be engineered according to standard protocols and produced that express genes encoding IL-2, IL-7, IL-15, IL-21, IL-12, IFN gamma, IFN beta, SDF-1, CCL23, CCL19, CCL1, CCL2, CCL17, CCL22 and/or CCL4 and combinations therefrom.

Transformed cells are selected and cultured further before harvesting for administration. All vectors can for example comprise of an antibiotic resistance gene, such as a puromycin resistance gene. Puromycin may therefore be used to select for transfected cells at a concentration of 0.1-1 µg/ml, or preferably 3-5 µg/ml. Prior to injection into the mice or other subjects, the cells are detached from the culture flasks, washed twice with PBS, and re-suspended in PBS, or other suitable buffer.

Suitable experiments may be performed in either an endogenous mouse breast cancer model (as described in WO2008150368) or an orthotopic pancreatic carcinoma model (as described in WO2010119039). In parallel experiments, mice with growing tumours are injected with the various engineered MSCs, either with or without T cells isolated from syngeneic subjects, and/or checkpoint inhibitors. After five days, the animals may be sacrificed and the tumours examined. Preliminary results indicate a reduction in tumour size/growth in subjects of the aforementioned treatment in comparison to appropriate controls.

Preparation of Human Mesenchymal Stem Cells:

In the present example, human MSCs are isolated from bone marrow by plastic adherence and are cultured in growth medium e.g. FBS containing DMEM as described by Pittinger, M. F. (2008) Mesenchymal stem cells from adult bone marrow, In D. J. Prockop, D. G. Phinney, B. A. Bunnell, Methods in Molecular Biology 449, Mesenchymal stem cells, Totowa: Humana Press).

Generation of Vectors for the Expression of Cytokines and Chemokine:

The transgene expression cassettes consisting a promoter and a gene (e.g. cDNA) for an immunostimulatory factor or factor supporting immune response are constructed using standard cloning techniques as described in Julia Lodge, Peter Lund, Steve Minchin (2007) Gene Cloning, New York: Tylor and Francis Group. The promoters may be constitutive promoters like the CMV promoter or the PGK promoter or inducible promoters like Tie2, RANTES or the HSP70 promoter.

Examples for genes encoding immunostimulatory factors or factors supporting immune responses are IL-2, IL-7, IL-15, IL-21, IL-12, IFN gamma, IFN beta, SDF-1, CCL23, CCL19, CCL1, CCL2, CCL17, CCL22 and/or CCL4 (Strengell et al., M, The Journal of Immunology, 2003, 170: 5464-5469; Borish et al., J Allergy Clin Immunol. 2003 February; 111(2 Suppl): S460-7). The gene may or may not be fused with tag-sequences (e.g. marker proteins/peptides like the hemagglutinin-tag or the HIS-tag) to allow easy detection of expression later on (Hinrik Garoff, 1985, Annual Review of Cell Biology, Vol. 1: 403-445).

The transgene is then inserted into a suitable vector system (e.g. lentiviral or gamma-retroviral vector) by standard cloning techniques. A suitable vector is for example described by Baum (EP 1757703 A2). The vector may or may not include a second transgene cassette consisting of a promoter and a selectable marker gene (cell surface marker or resistance gene, for example the pac gene to confer puromycin resistance) to allow enrichment of genetically modified cells later in the process (David P. Clark, Nanette J. Pazdernik, 2009, Biotechnology: Applying the Genetic Revolution, London: Elsevier).

Figure 2:
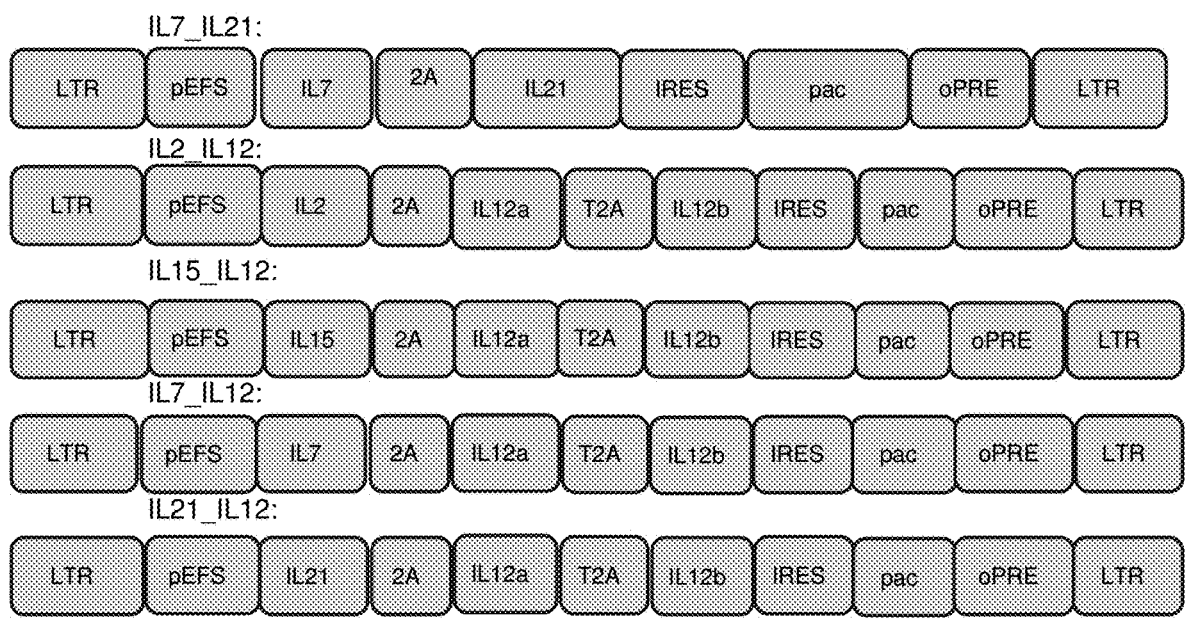
FIG. 2: Preferred viral expression constructs of the present invention. The constructs were cloned into a γ-retroviral backbone (pSERS11, EP2019134A1). All constructs are driven by the elongation factor short (pEFS) promoter. There are two Interleukins which are separated by a P2A. The α- & β-chain of IL-12 have to be separated by a T2A. Human Interleukin sequences are used (IL-2: GenBank: DQ861285.1, IL-7: GenBank: EF064721.1, IL-12α: GenBank: AF101062.1, IL-12β: NCBI Reference Sequence: NM_002187.2, IL-15: GenBank: AY720442.1, IL-21: GenBank: BC066260.1). A pac-gene and an oPRE-sequence are located behind an IRES-sequence. On the 5'- and 3'-end of the constructs are LTRs. The backbone contains LTRs, which are located on the 5'- & 3'-end of the constructs. The LTR at the 5'-end of the constructs contains a SV40 Enhancer, RSV promoter, R Region and U5 Region. The LTR at the 3'-end of the constructs has a deletion in the U3 Region, R Region, U5 Region and PolyA signal. The backbone contains a bacterial part: a lacZ promoter, an origin of replication, bla-gene and LacZ gene (pUC19).

Preferred constructs according to the present invention are shown in FIG. 2.

Genetic Modification of Mesenchymal Stem Cell:

The transduction is performed with modifications as described by Murray et al., 1999 Human Gene Therapy. 10(11): 1743-1752 and Davis et al., 2004 Biophysical Journal Volume 86 1234-1242. In detail:

6-well cell culture plates (e.g. Corning) are coated with Poly-L-Lysine (PLL) (e.g. Sigma-Aldrich, P4707-50ML): The PLL solution (0.01%) is diluted to final concentration between 0.0001% and 0.001% with PBS. 2 ml of the diluted PLL are used for each well. The plate is incubated at least for 2 h at room temperature. After incubation, the plates are washed carefully with PBS.

Viral vector supernatant in a final volume of 2 ml is added to each PLL-coated well. The number of particles should between 2×10e3 and 1×10e6 per well, which will result in multiplicity of infection of 0.25 and 10. The loaded plate is centrifuged for 2000×g, 30 min, 4° C. Afterwards the supernatant is discarded and 1×10e5 mesenchymal stem cells are seeded per well. The plates are incubated at 37° with 5% CO2 for further use.

Analysis of Transgene Expression in MSC:

Flow Cytometry:

To show that the immunostimulatory factors are expressed in the MSC intracellular flow cytometry assays are performed. 3 days after transduction MSC medium is exchanged for medium containing 1 µl BD Golgi Plug (Cat. No. 555029) per 1 ml Medium to enrich the expressed factors in the Golgi apparatus of the transduced cells. Cells are incubated for 16 h at 37° C. and are then immunostained for the expression of the factors. MSC are harvested and permeabilized using the BD Cytofix/Cytoperm Cell Permeabilization/Fixation Solution (Becton Dickinson, 554722) according to the manufacturer's instructions to allow intracellular staining of the target proteins. A hemagglutinin-tag specific antibody labelled with Phycoerythrin (PE) (Milteny, 120-002-687) is used for detection of the expressed factor. 2×10e5 MSC are stained with 100 µl of antibody (1:75 diluted with Perm/wash solution, Becton Dickinson, 554723). Alternatively, antibodies directly directed against the factor may be used according to the instruction of the manufacturer (e.g. anti-IL2 antibody labelled with PE, ebiosience 12-7029-41). The stained cells are washed and resuspended in PBS. The cells are then analysed on an FC500 flow cytometer (Beckman Coulter).

Figure 3:
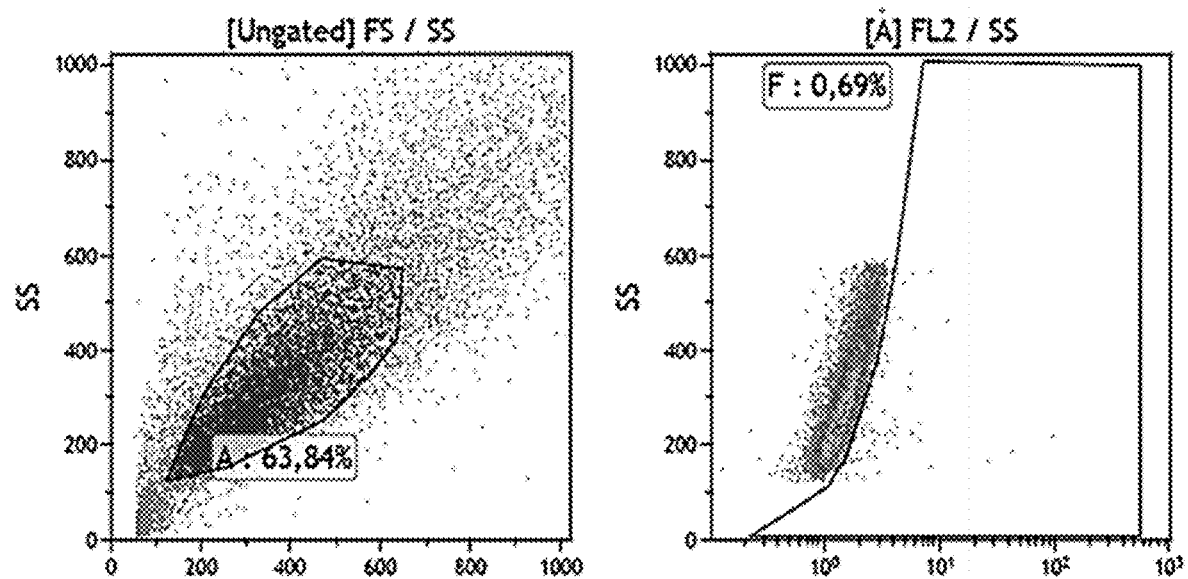
FIG. 3: Intracellular FACS (ic-FACS) sorting of cells transduced with viral expression constructs. Viral particles encoding the designated vectors were generated by transfection of 293T cells. Primary human MSCs were transduced with a MOI of 0.25. Transduced cells were selected with puromycin (Sigma Aldrich, P9620-10ML, 10 mg/mL, final conc.: 3 μg/mL). The selected cells were analysed by ic-FACS. To enhance detection of the expressed cytokines, cells were treated GolgiPlug (BD, 555029) for 16 h to enrich the proteins. Cells were permeabilized using (BD, 554722) according to instructions of manufacturer; afterwards an HA-Tag-specific antibody (Miltenyi, 130-092-257) was used to stain the cytokines (1.33 μL per staining). Cells were analysed by flow cytometry (FC500, Beckman coulter). (A): Non-transduced cells; (B): Construct comprising IL7 and IL21, replicate 1; (C): Construct comprising IL7 and IL21, replicate 2; (D): Construct comprising IL2 and IL12, replicate 1; (E): Construct comprising IL2 and IL12, replicate 2; (F): Construct comprising IL15 and IL12, replicate 1; (G): Construct comprising IL15 and IL12, replicate 2; (H): Construct comprising IL7 and IL12, replicate 1; (I): Construct comprising IL7 and IL12, replicate 2; (J): Construct comprising IL21 and IL12, replicate 1; and (K): Construct comprising IL21 and IL12, replicate 2.
Figure 3:
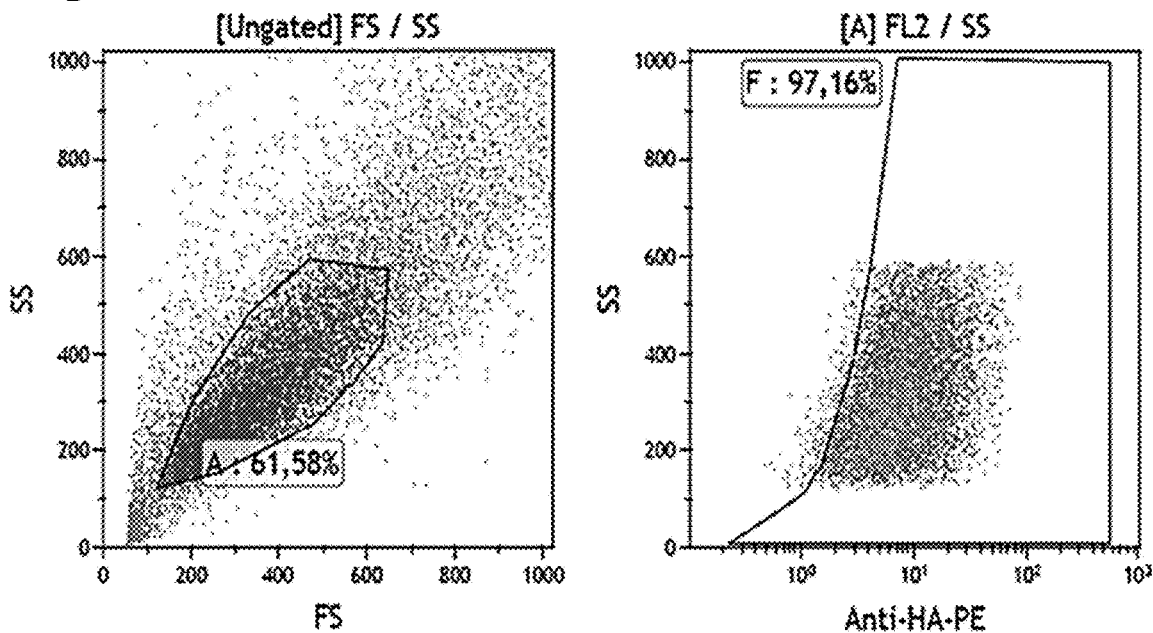
Figure 3:
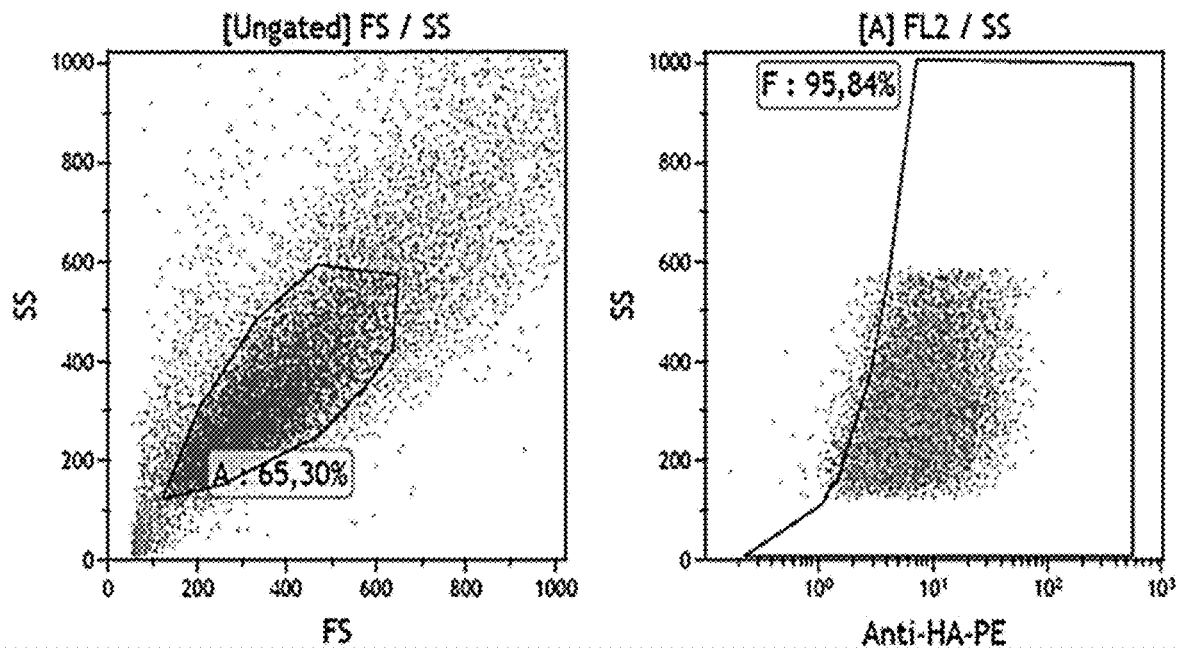
Figure 3:
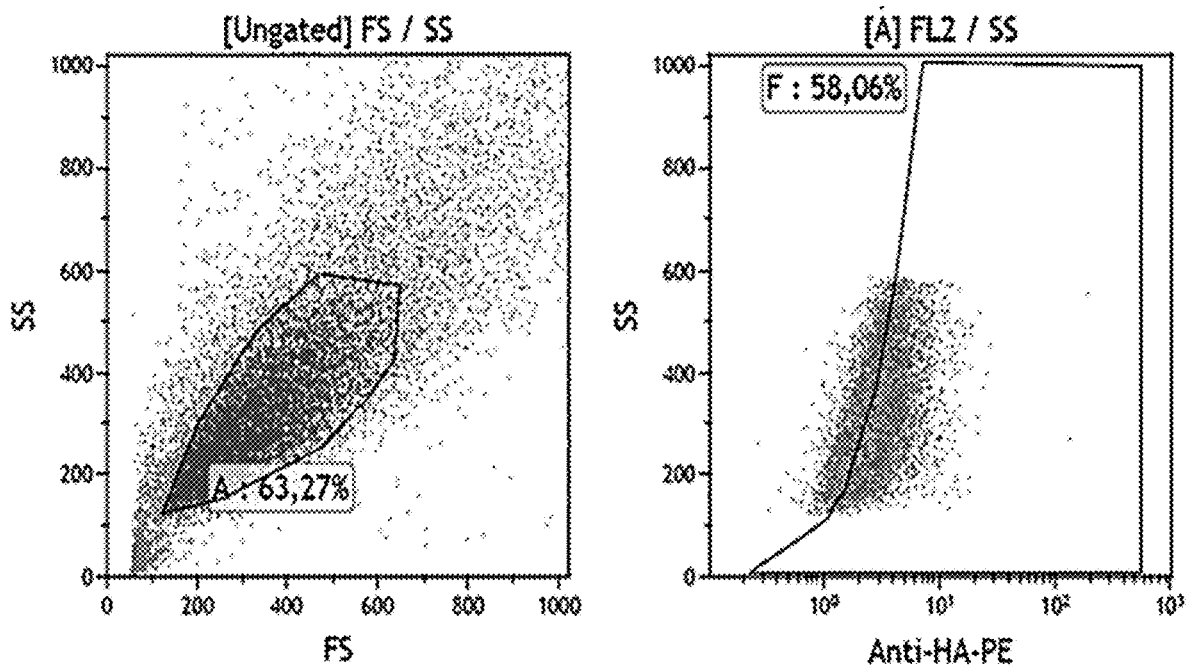
Figure 3:
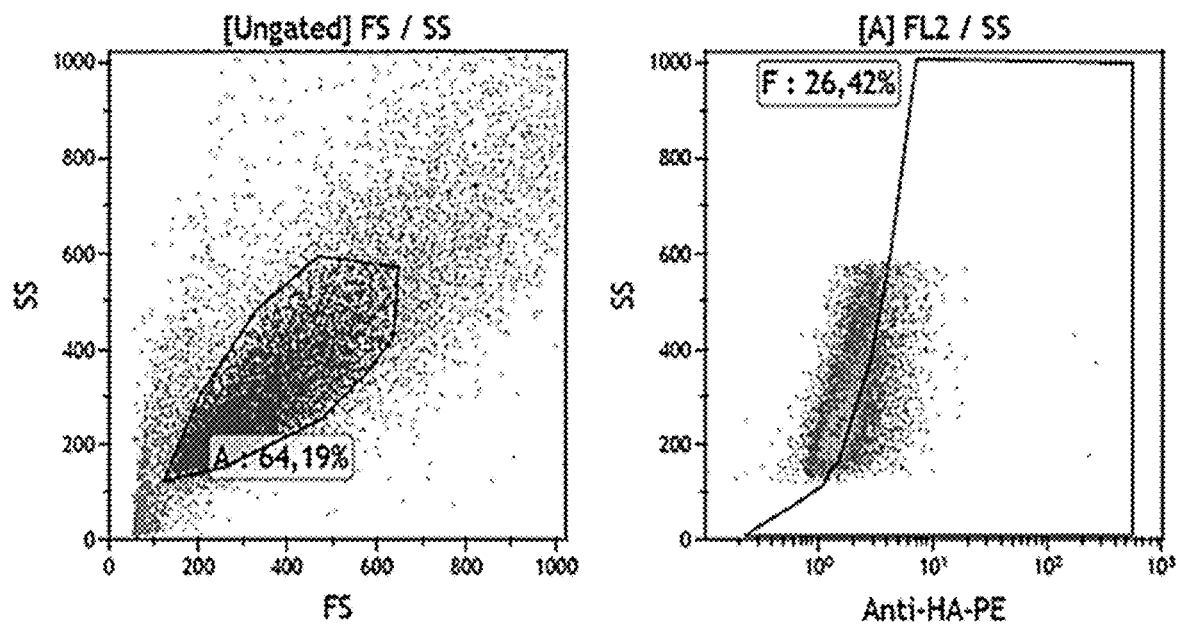
Figure 3:
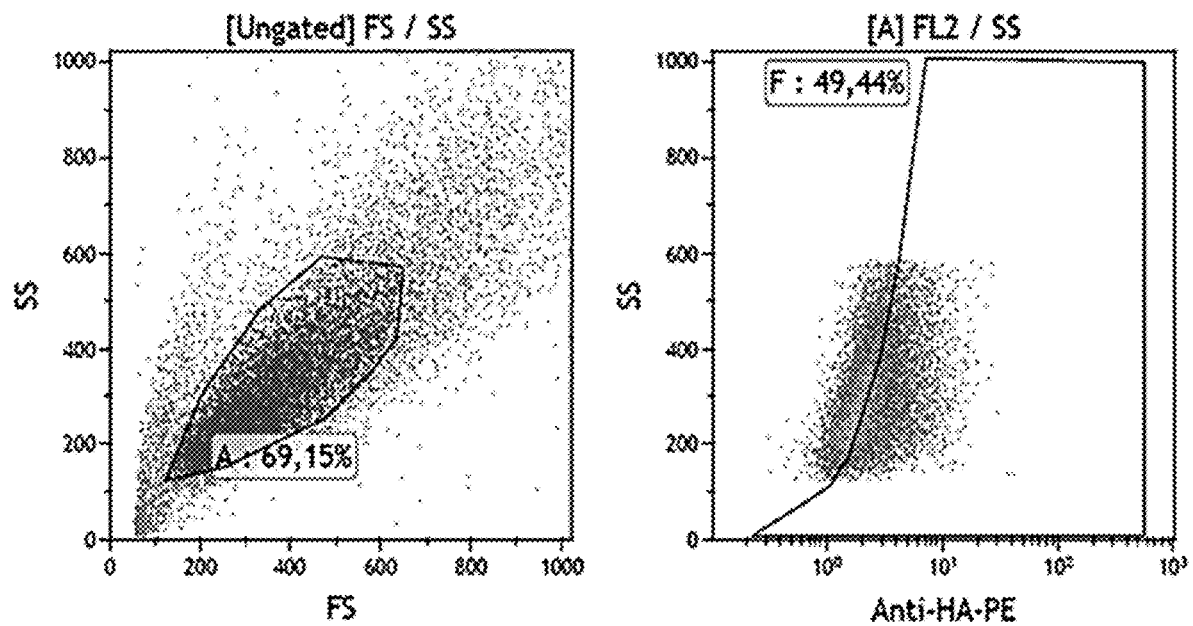
Figure 3:
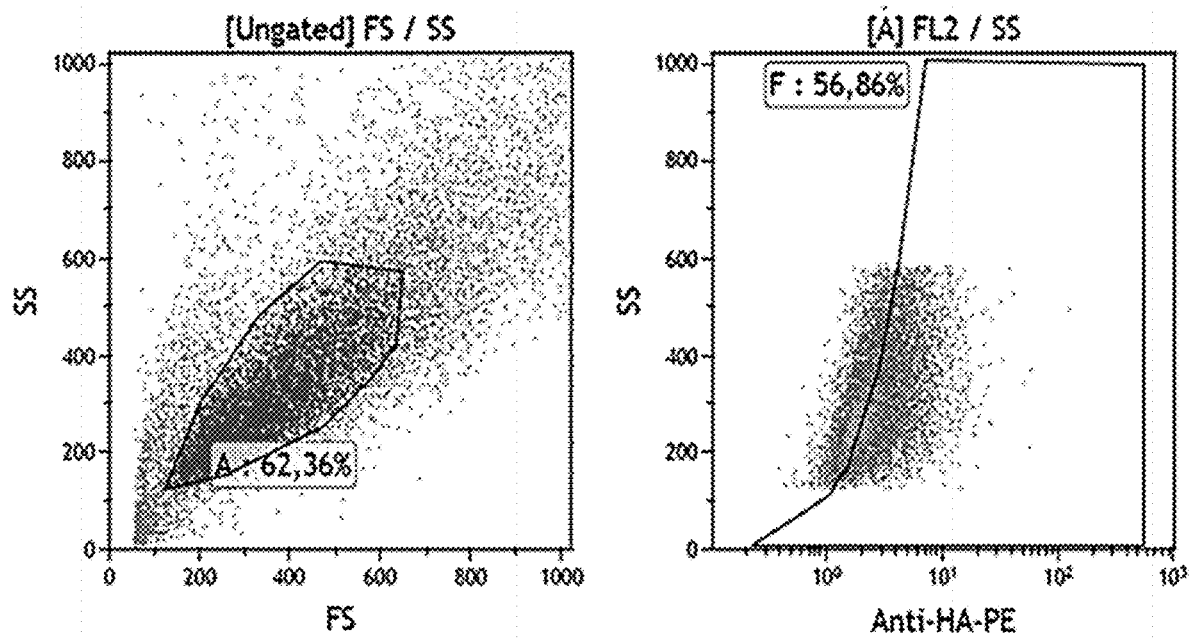
Figure 3:
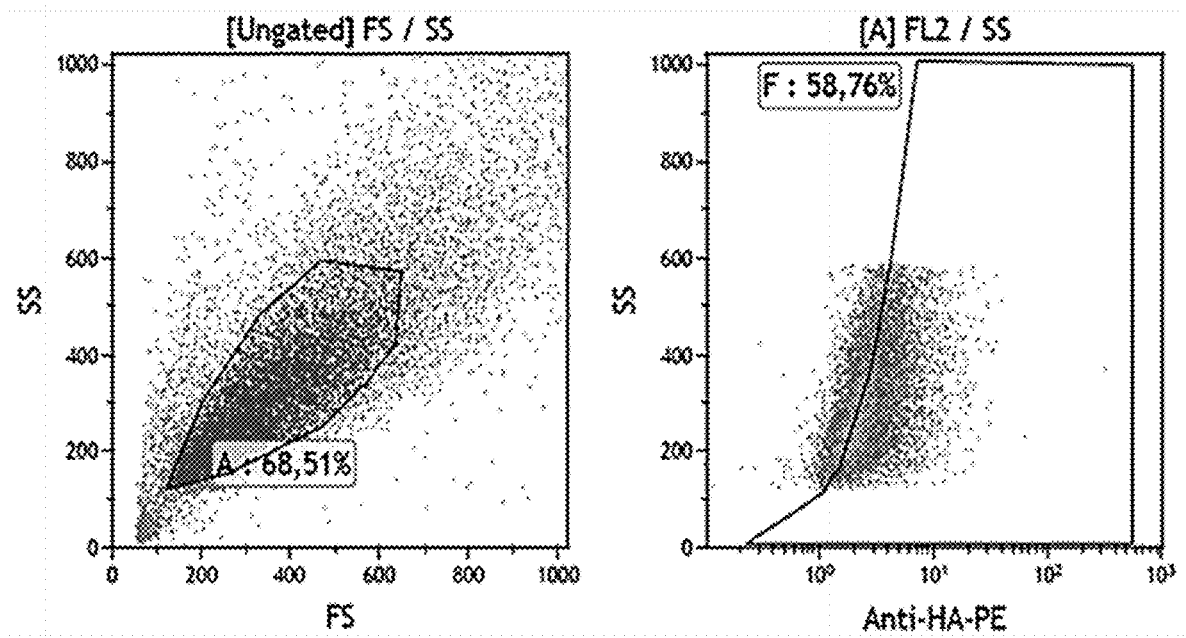
Figure 3:
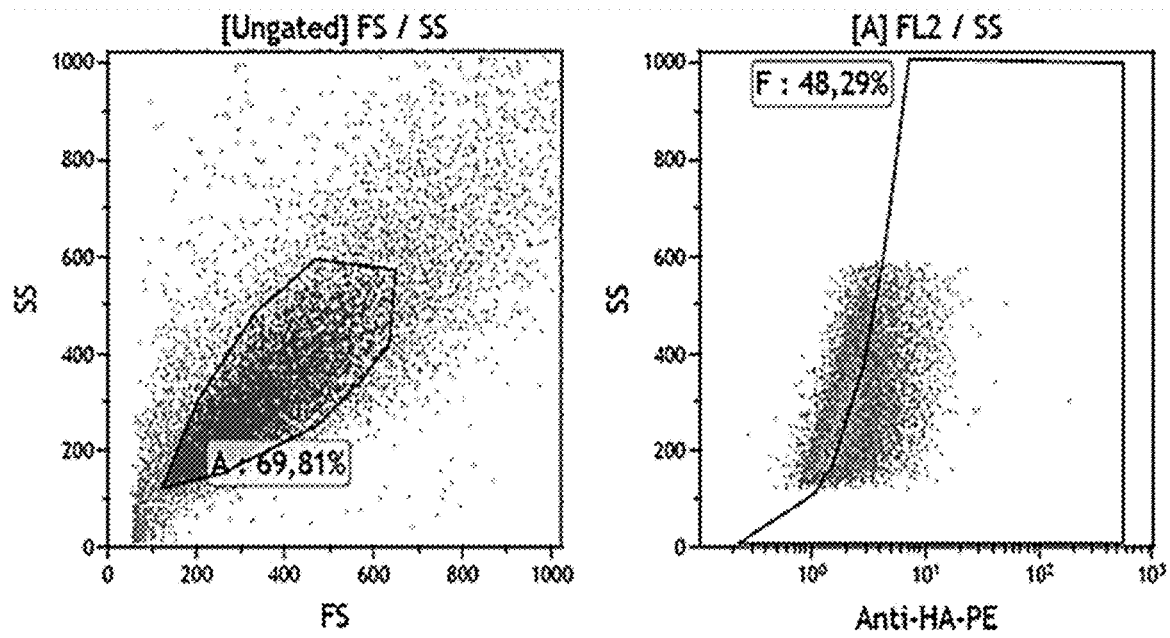
Figure 3:
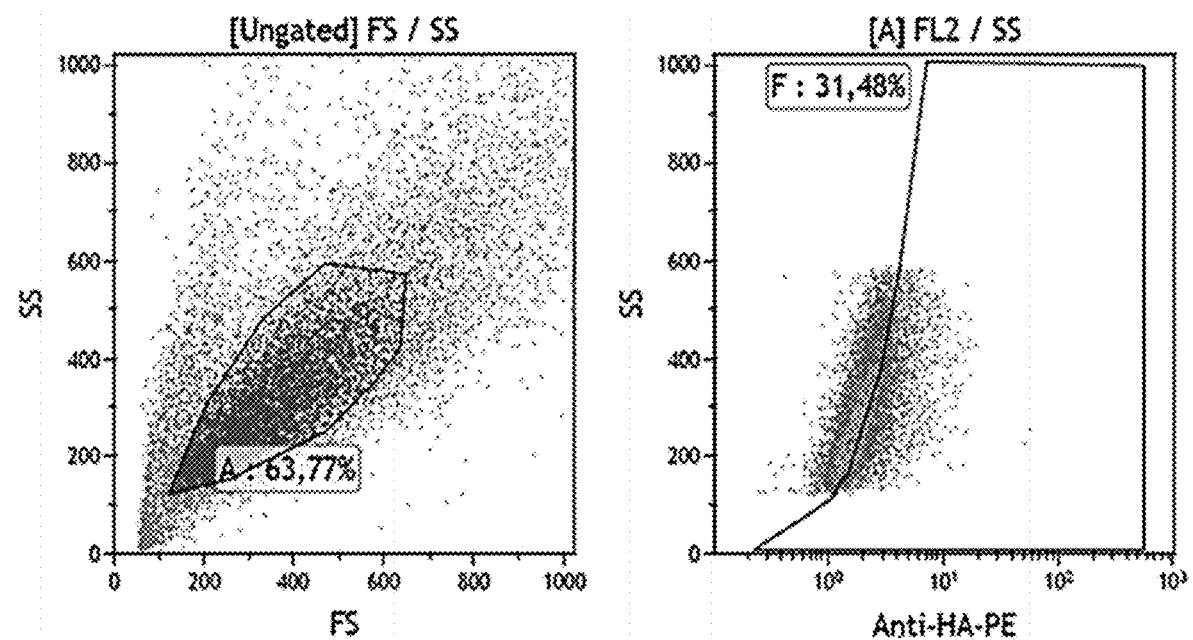
Figure 3:
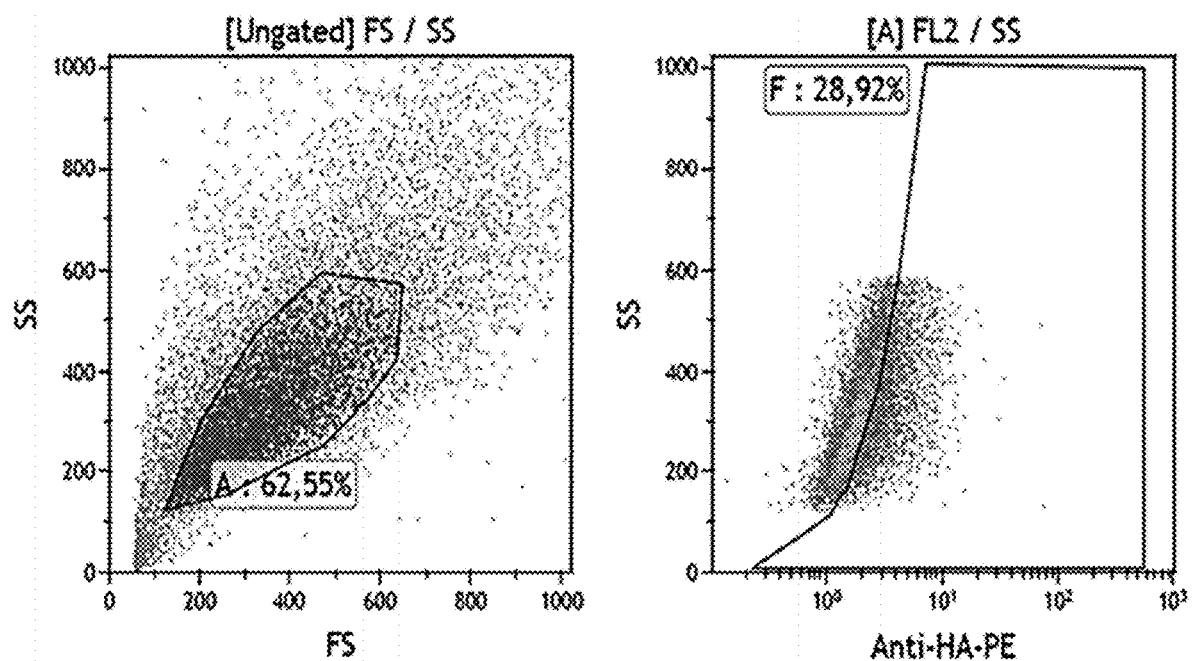

Expression of the cytokine transgenes are shown in FIG. 3.

ELISA:

Transduced MSC are seeded in 6 well plates (1×10e5 MSC per well). Transduced MSC, which carry the pac puromycin resistance gene, are enriched by puromycin selection. For this puromycin (3 µg/ml medium) is added to the medium and cells are cultivated over a period of 5 days at 37° C. and 5% CO2 with medium exchanges every 2 days to deplete non-transduced cells from the culture. Afterwards puromycin-free medium is used for the culture. MSC are reseeded at a defined cell number of 1×10e5 cells per well in a 6 well-plate and are incubated for 48 h. Medium is collected and used for immune factor specific ELISA for quantification according to the manufacturer's instructions (e.g. IL-7 ELISA: Thermo Scientific, EHIL7; IL-15 ELISA: Thermo Scientific, EHIL15).

Figure 4:
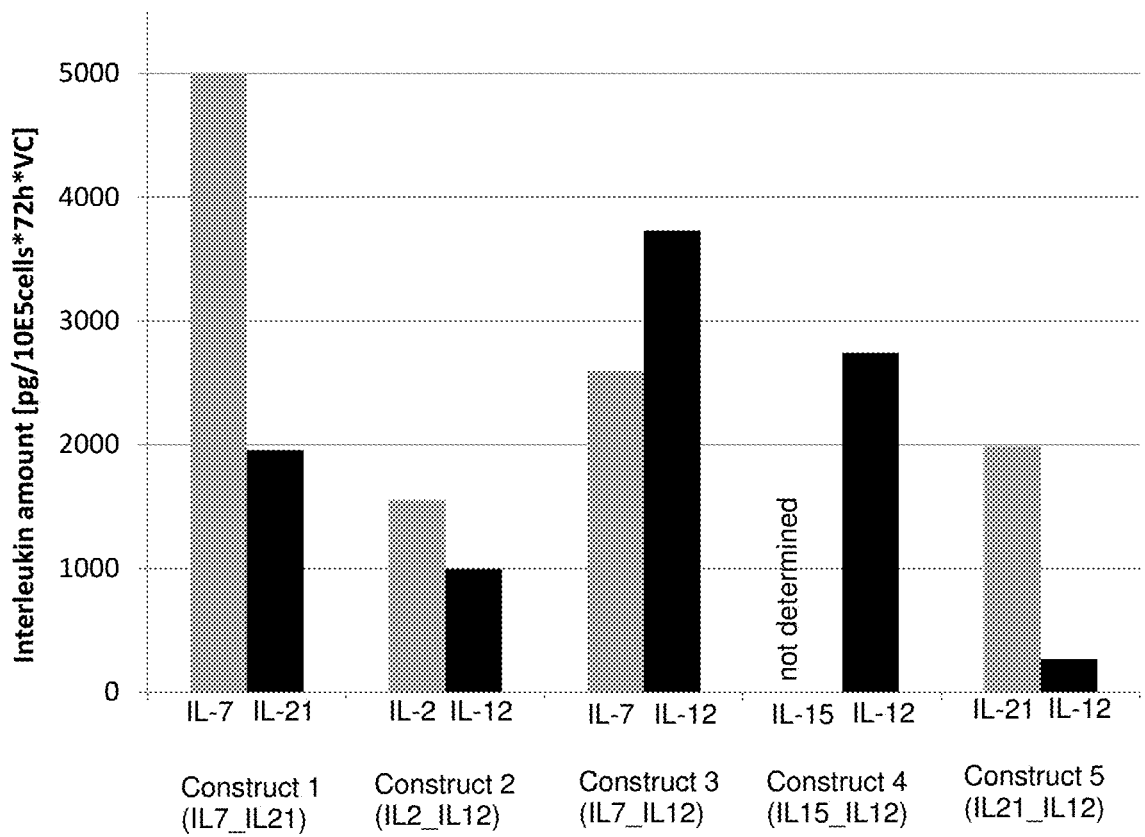
FIG. 4: ELISA detection of transgenic cytokines. Human MSC were transduced with the indicated constructs. The cells were Puromycin-selected cells and 1×10e5 cells seeded into 6-well plates. The supernatants were collected after 72 h and analysed by ELISA. The generated data were normalized to 10E5 cells and vector copy number. The used ELISA Kits were used according to the instructions of manufacturer: Human IL-2 (Thermo Scientific, EH21L2), Human IL-7 (Thermo Scientific, EHIL), Human IL-15 (BioLegend, 431707), Human IL-21 (Thermo Scientific, EHIL21).

Expression of the cytokine transgenes are shown in FIG. 4.

Monitoring of T Cell and Macrophage Activation In Vitro by ELISA:

Peripheral blood mononuclear cells (PBMC) are isolated from human blood using ficoll gradient centrifugation as described by Ivan J. Fuss, Marjorie E. Kanof, Phillip D. Smith, Heddy Zola, 2009 Curr. Protoc. Immunol. 85: 7.1.1-7.1.8. To assess the immune-stimulatory effect of the factors expressed in the MSC in vitro, co-culture assays are performed. 1-5×10e5 PBMC are seeded into a well of a 12-well together with 0.2-1×10e5 transduced MSC, untransduced MSC (control) or without MSC. Unspecific suboptimal stimulation of the T-cells in the culture mimicking engagement of the T cell receptor is performed: therefore, prior to cell seeding the wells of the plates may be coated with the stimulatory anti-CD3 antibody (e.g. OKT3, Janssen-Cilag). The antibody solution should have a concentration 0.5-0.1 µg/mL. Alternatively, PHA may be added to the coculture in concentration of 20 µg/ml (Ngoumou et al., Cytokine 25 (2004) 172-178). The wells are incubated at 37° C. and 5% CO2 for 2-5 days prior to analysis.

Compared to wells with untransduced MSC or wells without MSC, MSC transduced with immunostimulatory factors leads to an increased activation of the cultured T cells. Activation status of the T cells is assessed by measuring INF gamma concentration in the cultures as these cytokines are indicative for T cell activation (Boehm et al., Annu Rev Immunol. 1997; 15:749-95.). To assess activation status of monocytes, medium is collected and the release of tumour necrosis factor alpha (TNFa) is determined. Medium is collected and used for IFN gamma or TNF alpha specific ELISA for quantification according to the manufacturer's instructions (e.g. ELISA: IFN gamma, Thermo Scientific, EHIFNG; TNF alpha ELISA: Thermo Scientific, EH3TNFA).

Monitoring of T Cell and Macrophage Activation In Vitro by Flow Cytometry:

Peripheral blood mononuclear cells (PBMC) are isolated from human blood using ficoll gradient centrifugation as described by Ivan J. Fuss, Marjorie E. Kanof, Phillip D. Smith, Heddy Zola, 2009 Curr. Protoc. Immunol. 85: 7.1.1-7.1.8. To assess the immune-stimulatory effect of the factors expressed in the MSC in vitro, co-culture assays are performed. 1-5×10e5 PBMC are seeded into a well of a 12-well together with 0.2-1×10e5 transduced MSC, untransduced MSC (control) or without MSC. Unspecific suboptimal stimulation of the T-cells in the culture mimicking engagement of the T cell receptor is performed: therefore, prior to cell seeding the wells of the plates may be coated with the stimulatory anti-CD3 antibody (e.g. OKT3, Janssen-Cilag). The antibody solution should have a concentration 0.5-0.1 µg/mL. Alternatively, PHA may be added to the coculture in concentration of 20 µg/ml (Ngoumou et al., Cytokine 25 (2004) 172-178). The wells are incubated at 37° C. and 5% CO2 for 2-5 days prior to analysis.

Compared to wells with untransduced MSC or wells without MSC, MSC transduced with immunostimulatory factors lead to an increased activation of the cultured T cells and macrophages. Activation status of the T cells and macrophages is assessed by intracellular flow cytometry. 24 h prior to harvest of the cells, the cells are treated with medium containing 1 µl BD Golgi Plug (Cat. No. 555029) per 1 ml Medium. Afterwards cells are harvested and stained with fluorophore-labelled antibodies specific for T cells (e.g. anti-CD4, ebioscience 17-0048 or anti-CD8, ebioscience 9017-0087) or macrophages/monocytes (anti-CD14, ebioscience, 9017-0149) according to the manufacturer's instruction. Next cells are permeabilized using the BD Cytofix/Cytoperm Cell Permeabilization/Fixation Solution (Becton Dickinson, 554722) according to the manufacturer's instructions to allow intracellular staining of IFNg (ebioscience, 11-7319) or TNFa (ebioscience, 11-7349). Antibodies are used according to manufacturer's instructions. Afterwards cells are analysed using an FC500 flow cytometer (Beckman Coulter).

Monitoring of Anti-Tumoral Effect of MSC Administration in Animal Model:

Tumours from human tumour cell lines are grown in immune deficient mice (e.g. SCID mice) for 2 weeks and engineered MSCs are administered intravenously, for example via the tail vein. Following that, PBMCs are administered intravenously. The tumour sizes are then compared with the tumour sizes of untreated animals, or animals treated with MSCs only, or PBMCs only.

In another experiment, tumours from human tumour cell lines combined with engineered MSCs are grown in immune deficient mice (e.g. SCID mice) for 2 weeks and PBMCs are administered intravenously. The tumour sizes are then compared with the tumour sizes of untreated animals, or animals treated with MSCs only, or PBMCs only.

The above experiments can be performed whereas instead of PBMCs, purified cytotoxic T Lymphocytes (CTLs) are used, or CART cells that carry CARs directed at tumour antigens present on the tumours. Likewise, a checkpoint inhibitor (e.g. anti-PD-1, or anti-PD-L1 antibody) can be used together with MSCs and PBMCs, or MSCs and CTLs, or MSCs and CARTs.

The tumours from the above experiments are analysed histologically to assess the amount of expression of the cytokines and cytokine combinations by MSCs, by using antibodies reactive against these cytokines. The extent of infiltration of the tumour by PBMCs, CTLs and CARTs is assessed using a hematoxylin and eosin dye (H&E). The extent of infiltration of the tumour by T cells can be assessed by using immunohistochemistry with antibodies against CD3. The extent of infiltration of the tumour by monocytes can be assessed by using immunohistochemistry with antibodies against CD19. The extent of activation of the infiltrating T cells in the tumour can be assessed by using immunohistochemistry with antibodies against CD69, as well as IFN-gamma.

To confirm the experiments above, these experiments are repeated with different types of tumours, grown using different human tumour cell lines and CARTs with specificity against respective tumour-associated antigens.

What is claimed is:

1. A method of treating a tumor in a subject comprising administering a genetically modified mesenchymal stem cell (MSC) to the subject, wherein said MSC comprises one or more exogenous nucleic acid molecule(s), wherein said one or more exogenous nucleic acid molecule(s) comprises one or more regions encoding two or more immune response-stimulating cytokines operably linked to one or more promoters or promoter/enhancer combinations, wherein the two or more immune response-stimulating cytokines comprise IL-7 and IL-12, wherein the treatment leads to support and/or strengthening of an anti-tumour immune response in the subject.

2. The method according to claim 1, wherein the one or more exogenous nucleic acid molecule(s) encodes additionally at least one immune response-stimulating cytokine selected from the group consisting of IL-15, IL-21, IFN gamma and IFN beta.

3. The method according to claim 1, wherein the promoter or promoter/enhancer combination yields constitutive expression of the exogenous nucleic acid.

4. The method according to claim 1, wherein the promoter yielding constitutive expression is an EF1alpha promoter, a PGK promoter, a CMV promoter, an SV40 promoter, a GAG promoter or a UBC promoter.

5. The method according to claim 1, wherein the one or more exogenous nucleic acid molecule(s) comprises a region encoding an additional immune stimulatory molecule that induces T-cell proliferation and/or differentiation operably linked to a promoter or promoter/enhancer combination.

6. The method according to claim 5, wherein the additional immune stimulatory molecule that induces T-cell proliferation and/or differentiation is CD28.

7. The method according to claim 1, wherein the one or more exogenous nucleic acid molecule(s) further comprises a region encoding a chemokine with chemotactic properties for attracting T cells, selected from the group consisting of chemokine (C-C motif) ligand 1 (CCL1), CCL2, CCL4, CCL17, CCL19, CCL22, CCL23, and stromal cell-derived factor 1 (SDF-1).

8. The method according to claim 1, wherein the promoter or promoter/enhancer combination is induced when the genetically modified mesenchymal stem cell comes into proximity with a tumor tissue or a tumor stromal tissue, or wherein the promoter or promoter/enhancer combination is induced upon differentiation of said cell, post-administration.

9. The method according to claim 1, wherein the promoter is the RANTES promoter, the HSP70 promoter or the Tie2 promoter.

10. The method according to claim 1, wherein the immune response-stimulating cytokine maintains or enhances the activity, survival and/or number of immune cells within and/or in proximity to a tumor tissue.

11. The method according to claim 1, wherein the method additionally comprises administering an anti-tumor immunotherapy to the subject.

12. The method according to claim 11, wherein the anti-tumor immunotherapy comprises the administration of an immune cell.

13. The method according to claim 12, wherein the mesenchymal stem cell and the immune cell are autologous to the subject of medical treatment.

14. The method according to claim 12, wherein the immune cell is a T cell.

15. The method according to claim 12, wherein the immune cell is a T cell comprising an artificial T cell receptor, wherein said T cell receptor binds specifically to a tumor antigen.

16. The method according to claim 12, wherein the immune cell is a macrophage.

17. The method according to claim 11, wherein the anti-tumor immunotherapy comprises the administration of one or more checkpoint inhibitors.

18. The method according to claim 17, wherein said checkpoint inhibitor is a PD-L1 inhibitor, PD-1 inhibitor and/or CTLA-4 inhibitor.

19. The method according to claim 11, wherein the anti-tumor immunotherapy comprises administration of tumor antigens or patient-derived tumor material.

20. The method according to claim 11, wherein the anti-tumor immunotherapy comprises the administration of an antibody or antibody fragment targeted to a tumor-specific antigen.

* * * * *